United States Patent [19]
Kakimoto et al.

[11] Patent Number: 5,093,255
[45] Date of Patent: Mar. 3, 1992

[54] ACID UREASE AND PRODUCTION THEREOF

[75] Inventors: Shigeya Kakimoto, Kawanishi; Yasuhiro Sumino, Kobe; Takashi Suzuki, Takatsuki, all of Japan

[73] Assignee: Takeda Chemical Industries, Ltd., Osaka, Japan

[21] Appl. No.: 217,355

[22] Filed: Jul. 11, 1988

[30] Foreign Application Priority Data

Jul. 9, 1987 [JP] Japan .................. 62-171750
Apr. 14, 1988 [JP] Japan .................. 63-92356

[51] Int. Cl.$^5$ .................. C12N 9/00; C12N 9/14; C12N 9/78
[52] U.S. Cl. .................. 435/183; 435/227; 435/195; 435/252.9; 435/253.4; 435/803; 435/814; 435/853; 435/885
[58] Field of Search ............ 435/183, 227, 195, 252.9, 435/253.4, 803, 814, 853, 885

[56] References Cited
FOREIGN PATENT DOCUMENTS 0266088 5/1988 European Pat. Off. ........... 426/11
0280398 8/1988 European Pat. Off. ........... 435/227
20830 5/1981 Japan ................................. 426/12

OTHER PUBLICATIONS

Chemical Abstracts, vol. 87, 1977, 87:18656z.
Chemical Abstracts, vol. 84, 1976, 84:147308z.
Chemical Abstracts, vol. 77, 1972, 45436c.
Chemical Abstracts, vol. 106, 1987, 106:174596w.
Suzuki et al., Applied and Environmental Microbiology, Mar. 1979, pp. 379–382.
Moreau et al., Infection and Immunity, Jan. 1976, pp. 9–15.
Takabe et al., The Poster Abstract of The Japanese-United States Congress of Pharmaceutical Sciences, Dec. 2–7, 1987, Honolulu, Hawaii, Poster Session J-2 Microbial Science, J6-X-9.
Kakimoto et al., Abstracts of the 1988 year Annual Meeting of the Society of Japanese Agricultural Chemistry, p. 322, 3Qp10.

Primary Examiner—Ronald W. Griffin
Assistant Examiner—Pamela S. Webber
Attorney, Agent, or Firm—Wenderoth, Lind & Ponack

[57] ABSTRACT

A novel urease having an optimal pH for activity in the acidic region is produced by a microorganism belonging to the genus Lactobacillus or Streptococcus. The urease is superior to the conventional urease in pH stability, temperature stability and alcohol stability.

12 Claims, 16 Drawing Sheets

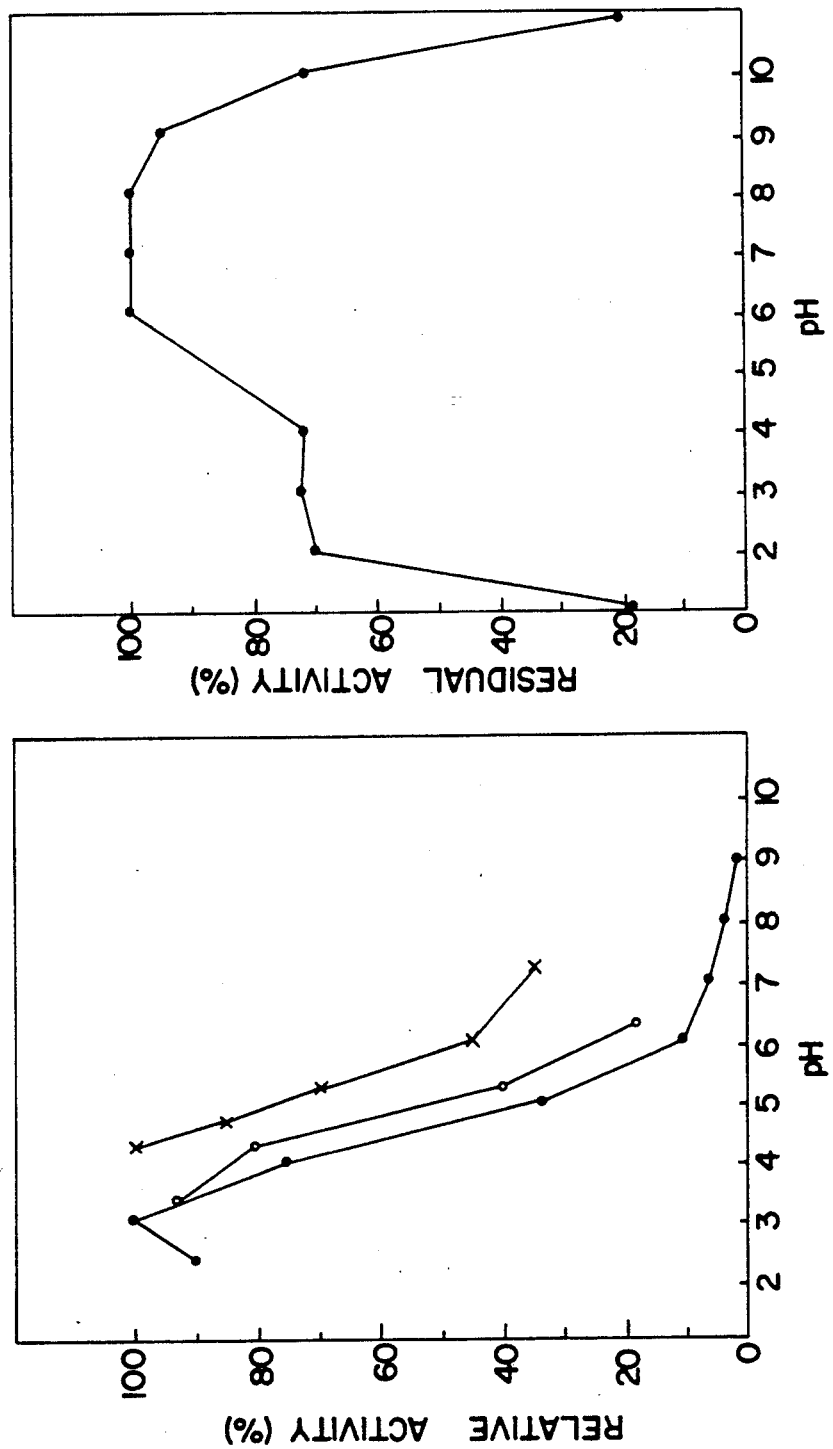

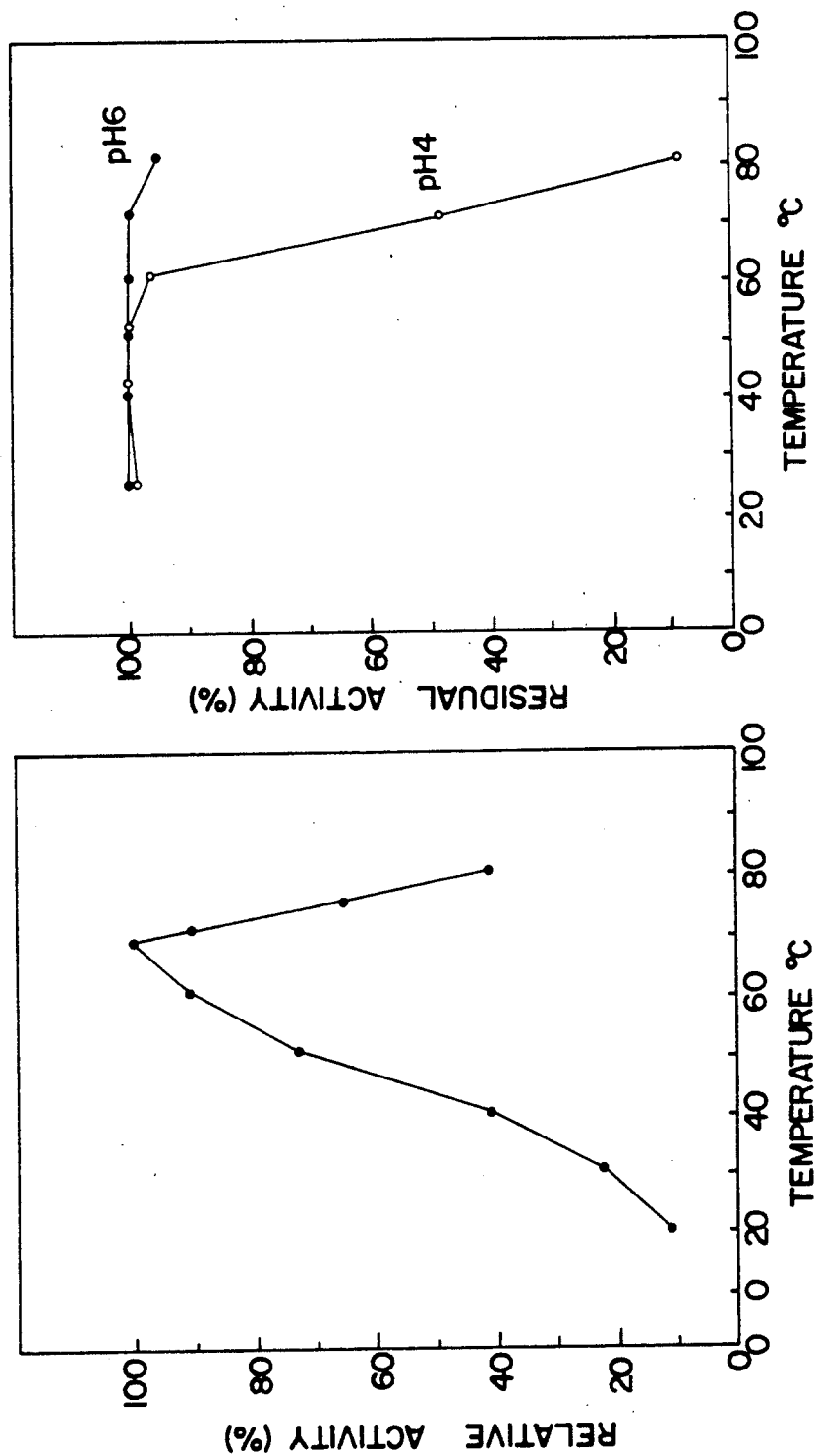

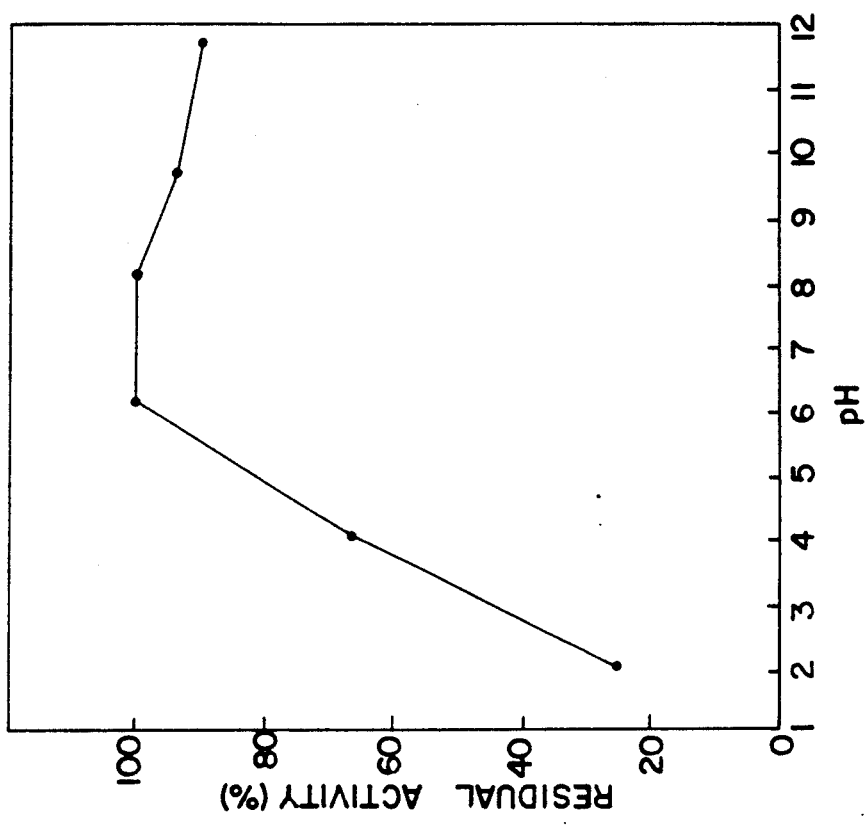
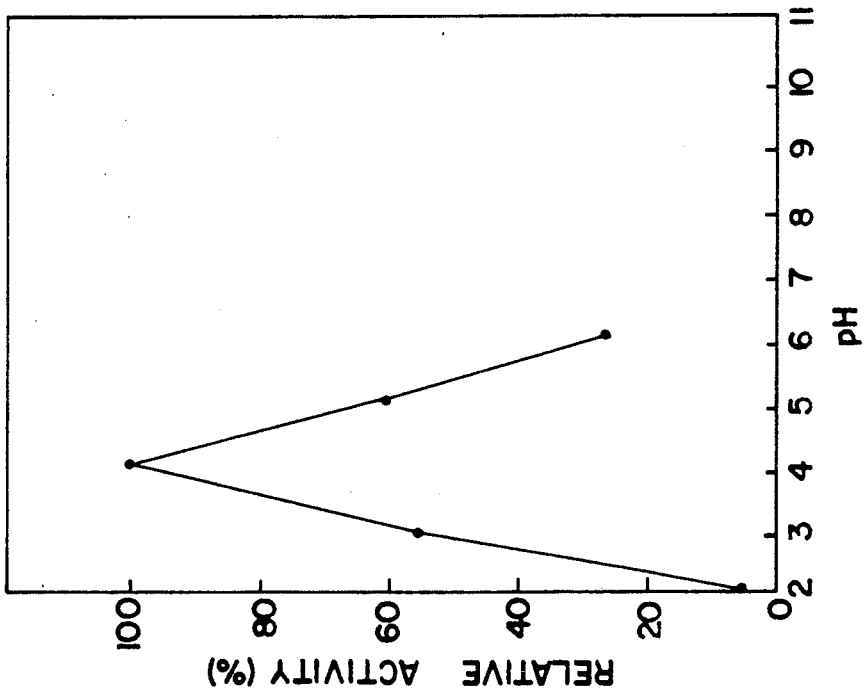

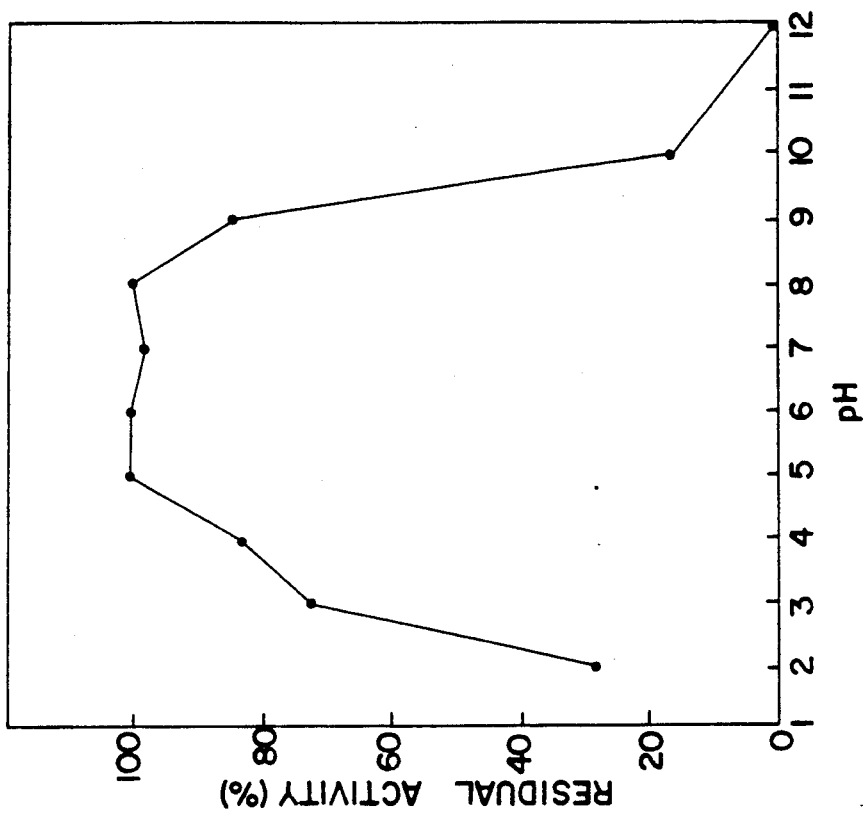
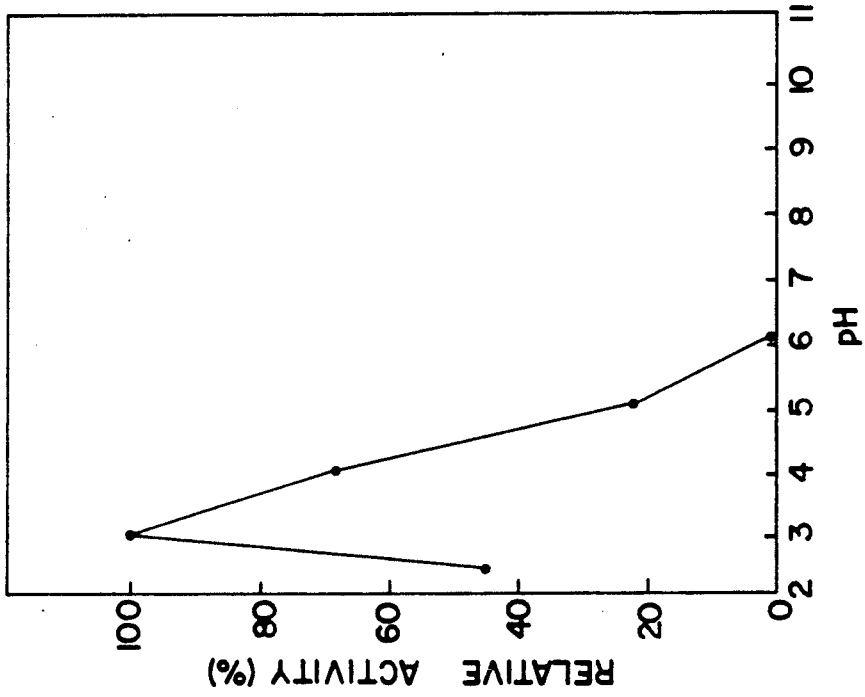

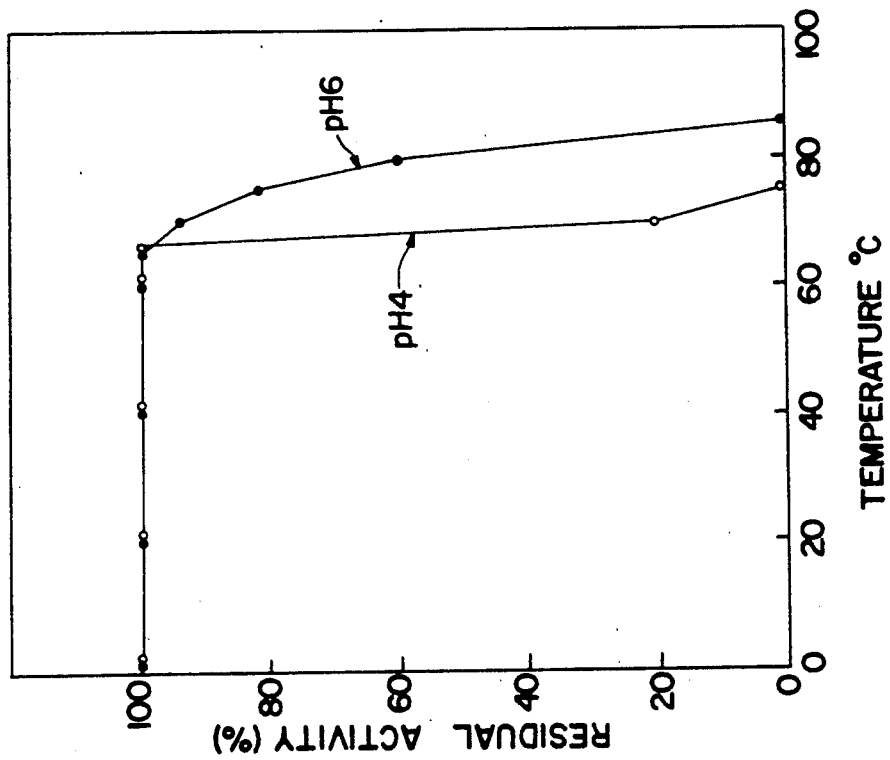
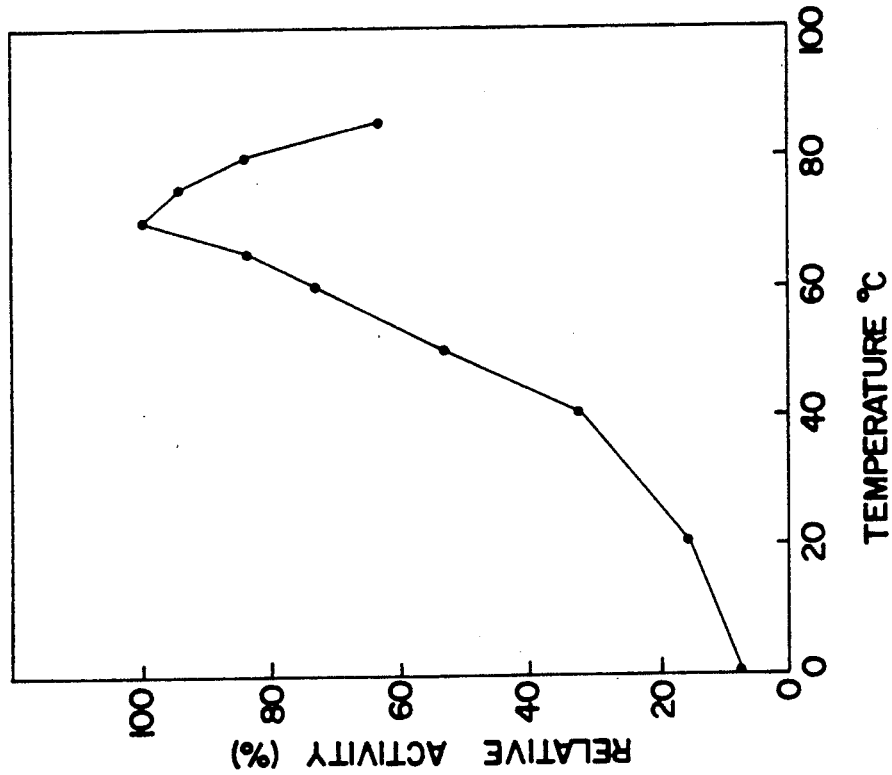

ACID UREASE AND PRODUCTION THEREOF

The present invention relates to a novel urease which is of use as an enzyme for improving the quality of alcoholic liquors or for assay of urea in clinical laboratory examination or food.

Urease (E. C. 3. 5. 1. 5) is the enzyme which decomposes urea into ammonia and carbon dioxide gas and is broadly distributed in the natural kingdom covering plants, animals and microorganisms. In addition to the ureases from *Canavalia adans* (Jack bean) and *Bacillus pasteurii* which have been commercially produced and put to use, there also are known the urease having a molecular weight of about 440,000 which is elaborated by microbial strains of *Corynebacterium lilium, Brevibacterium ammoniagenes, Arthrobacter paraffineus, Proteus vulgaris, Microbacterium ammoniaphilum* or *Bordetella bronchiseptica* (Japanese Patent Publication No. 60-55119), the urease having a molecular weight of about 440,000 as elaborated by Bacillus sp. UR-155 [Japanese Unexamined Patent Publication (KOKAI) 59-17987] and the urease having a molecular weight of about 280,0000 as elaborated by *Pseudomonas aeruginosa* and *Nocardia erythropolis* [Japanese Unexamined Patent Application (KOKAI) 61-257183].

All the above-mentioned ureases have optimal reaction pH values in the neutral to alkaline region and not only are labile and tend to be deactivated on the acidic side but undergo reaction only with difficulty. Especially where the reaction temperature is above room temperature or in a reaction system containing an organic solvent such as alcohol, these ureases show the drawback of considerable inactivation.

The present inventors made an intensive screening investigation for finding a microorganism capable of producing a urease which would have an optimal pH in the acidic region and be highly stable and found that a strain belonging to the genera Lactobacillus and Streptococcus accumulates a desirable urease within their cells. The inventors then isolated and purified this enzyme, conducted a further investigation and arrived at the present invention.

An object of the present invention is therefore to provide a novel urease having the following physicochemical properties and having an optimal pH in the acidic region (hereinafter referred to briefly as the acid urease):

(1) Action

It produces 2 moles of ammonia and 1 mole of carbon dioxide gas from 1 mole of urea and 1 mole of water.

(2) Substrate specificity

It acts most potently on urea.

(3) Optimal pH and pH stability

Its optimal pH is 1.5 to 5.5; it is stable at pH 6–8 at 37° C. for 30 minutes.

(4) Optimal temperature and temperature stability

Its optimal temperature at the optimal pH is 55° to 75° C.; at pH 6 it remains stable for 30 minutes up to 50° C.

(5) Inhibitors

It is inhibited by mercuric chloride and acetohydroxamic acid.

(6) Molecular weight

Its molecular weight as determined by gel filtration is 100,000 to 250,000.

(7) Specific activity

Its specific activity at the optimal pH and 37° C. is not less than 20 U/mg protein.

Another object of the present invention is to provide a method for producing an acid urease by cultivating in a culture medium a microorganism which belongs to the genus Lactobacillus or Streptococcus. As the microorganisms used in producing the acid urease of this invention, the novel urease-producing strains of the genus Lactobacillus or Streptococcus can be mentioned. Specifically, *Lactobacillus fermentum* JCM 5867 (IFO 14511, FERM P-8990), *Lactobacillus fermentum* JCM 5868 (IFO 14512, FERM P-8991), *Lactobacillus fermentum* JCM 5869 (IFO 14513, FERM P-8992), *Lactobacillus reuteri* UM-12 (IFO 14629, FERM P-9456), *Lactobacillus reuteri* UM-18 (IFO 14630, FERM P-9457), *Lactobacillus reuteri* Rt-5 (IFO 14631, FERM P-9458), *Lactobacillus ruminis* PG-98 (IFO 14632, FERM P-9459) *Streptococcus mitior* PG-154 (IFO 14633, FERM P-9460), *Streptococcus bovis* PG-186 (IFO 14634, FERM P-9461) and *Streptococcus salivarius* PG-303W (IFO 14746) may be mentioned as examples. The IFO numbers quoted above are deposit numbers at Institute for Fermentation, Osaka (IFO) 17-85, Juso-honmachi 2-chome, Yodogawa-ku, Osaka 532, Japan and the FERM P numbers are deposit numbers at the Fermentation Research Institute (FRI), Agency of Industrial Science and Technology, the Ministry of International Trade and Industry, 1-3, Higashi 1-chome, Tsukuba-shi, Ibaraki-ken 305, Japan.

*Lactobacillus fermentum* JCM 5867 (IFO 14511), *Lactobacillus fermentum* JCM 5868 (IFO 14512) and *Lactobacillus fermentum* JCM 5869 (IFO 14513) are known strains listed on Research communications (No. 13, page 94, 1987) issued from IFO.

These microorganisms, which were deposited at FRI on the date of the following Table, have been converted to a deposit under the Budapest Treaty and stored at FRI under the accession numbers of FERM BP as shown in the following Table.

| Microorganism | Date of deposit at FRI | Accession Number under the Budapest Treaty |
| --- | --- | --- |
| Lactobacillus fermentum JCM 5867 | October 4, 1986 | FERM BP-1454 |
| Lactobacillus fermentum JCM 5868 | October 4, 1986 | FERM BP-1445 |
| Lactobacillus fermentum JCM 5869 | October 4, 1986 | FERM BP-1446 |
| Lactobacillus reuteri UM-12 | July 7, 1987 | FERM BP-1904 |
| Lactobacillus reuteri UM-18 | July 7, 1987 | FERM BP-1905 |
| Lactobacillus reuteri Rt-5 | July 7, 1987 | FERM BP-1447 |
| Lactobacillus ruminis PG-98 | July 7, 1987 | FERM BP-1906 |
| Streptococus mitior PG-154 | July 7, 1987 | FERM BP-1448 |
| Streptococcus bovis PG-186 | July 7, 1987 | FERM BP-1449 |

The strain PG-303W has been deposited at FRI as of Apr. 14, 1988 as FERM BP-1856.

The bacteriological characteristrics of *Lactobacillus reuter* UM-12, *Lactobacillus reuteri* UM-18, *Lactobacillus reuteri* Rt-5 and *Lactobacillus ruminis* PG-98 are described below.

| Strain | UM-12 | UM-18 | Rt-5 |
|---|---|---|---|
| Origin | Mouse stool | Mouse stool | Rat stool |
| Cell morphology | Short rod<br>(0.6–0.8 × 1.0–15) | Short rod<br>(0.6–0.8 × 1.0–15) | Short rod<br>(0.6–0.8 × 1.0–15) |
| Motility | − | − | − |
| Sporulation | − | − | − |
| Gram stain | + | + | + |
| Oxygen demand | Microaerophile | Microaerophile | Facultative anaerobe |
| Oxidation-fermentation test | Fermentative | Fermentative | Fermentative |
| Fermentation type | Heterofermentative,<br>DL-lactic acid | Heterofermentative,<br>DL-lactic acid | Heterofermentative,<br>DL-lactic acid |
| Catalase | − | − | − |
| Oxidase | − | − | − |
| Reduction of nitrate | − | − | − |
| Liquefaction of gelatin | − | − | − |
| Hydrolysis of starch | − | − | − |
| Decomposition of esculin | − | − | − |
| MR test | + | + | + |
| VP test | − | − | − |
| Production of indole | − | − | − |
| Production of hydrogen sulfide | − | − | − |
| Production of $NH_3$ from arginine | + | + | + |
| Litmus milk | Acid produced | Acid produced | Acid produced |
| Production of gas from glucose | + | + | + |
| Optimum temperature for growth °C. | 25–45 | 30–45 | 25–45 |
| Growth at 45° C. | + | + | + |
| Growth at 15° C. | − | − | − |
| Growth at pH 4.0 | + | + | + |
| Growth at pH 9.6 | − | − | − |
| Growth in presence of 3% NaCl | + | − | + |
| Growth in presence of 6.5% NaCl | − | − | − |
| Production of acid | | | |
| Adonitol | − | − | − |
| Arabinose | + | − | − |
| Arabitol | − | − | − |
| Arbutin | − | − | − |
| Cellobiose | − | − | − |
| Dulcitol | − | − | − |
| Fructose | − | − | − |
| Galactose | + | + | + |
| Gluconate | + | + | + |
| Glucose | + | + | + |
| Glycerol | − | − | − |
| Inositol | − | − | − |
| Inulin | − | − | − |
| Lactose | + | + | + |
| Maltose | + | + | + |
| Mannitol | − | − | − |
| Mannose | − | − | − |
| Melezitose | − | − | − |
| Melibiose | + | + | + |
| α-Methylglucoside | − | − | − |
| Raffinose | + | + | + |
| Rhamnose | − | − | − |
| Ribose | + | − | +(weakly) |
| Salicin | − | − | − |
| Sorbitol | − | − | − |
| Sorbose | − | − | − |
| Starch | − | − | − |
| Sucrose | + | + | + |
| Trehalose | − | − | − |
| Xylose | + | − | − |
| Xylitol | − | − | − |
| Auxotrophy | | | |
| Niacin | + | + | + |
| Thiamine | + | + | + |
| Choline chloride | − | + | − |
| Riboflavin | + | − | − |
| Ca-Pantothenate | + | + | + |
| Pyridoxal | − | + | − |
| Folic acid | − | − | − |
| GC content (%) of DNA | 39.8 | 40.7 | 40.3 |
| Peptidoglycan type | Lys<br>Asp<br>Ala<br>Glu | Lys<br>Asp<br>Ala<br>Glu | Lys<br>Asp<br>Ala<br>Glu |

The bacteriological characteristics of *Lactobacillus ruminis* PG-98 are as follows.

| | |
|---|---|
| Origin | Swine cecum |
| Cell morphology | Short rod (0.6–0.8 × 1.0–15) |
| Motility | – |
| Sporulation | – |
| Gram stain | + |
| Oxygen demand | Microaerophilic |
| Oxidation-fermentation test | Fermentative |
| Fermentation type | homo L-lactic acid |
| Catalase | – |
| Oxidase | – |
| Reduction of nitrate | – |
| Liquefaction of gelatin | – |
| Hydrolysis of starch | +(weakly) |
| Decomposition of esculin | + |
| MR test | +(weakly) |
| VP test | – |
| Production of indole | – |
| Production of hydrogen sulfide | – |
| Production of $NH_3$ from arginine | – |
| Litmus milk | No change |
| Production of gas from glucose | – |
| Optimum temperature for growth, °C. | 30–37 |
| Growth at 45° C. | – |
| Growth at 15° C. | – |
| Growth at pH 4.0 | – |
| Growth at pH 9.6 | – |
| Growth in presence of 3% NaCl | – |
| Growth in presence of 6.5% NaCl | – |
| α-Hemolysis | – |
| β-Hemolysis | – |
| Production of acid | |
| Adonitol | – |
| Arabinose | – |
| Arabitol | – |
| Arbutin | – |
| Cellobiose | + |
| Dulcitol | – |
| Fructose | + |
| Galactose | + |
| Gluconate | – |
| Glucose | + |
| Glycerol | – |
| Inositol | – |
| Inulin | – |
| Lactose | – |
| Maltose | + |
| Mannitol | – |
| Mannose | + |
| Melezitose | – |
| Melibiose | – |
| α-methylglucoside | – |
| Raffinose | + |
| Rhamnose | – |
| Ribose | – |
| Salicin | + |
| Sorbitol | – |
| Sorbose | – |
| Starch | + |
| Sucrose | + |
| Trehalose | – |
| Xylose | – |
| Xylitol | – |
| GC content (%) of DNA | 45.6 |
| Peptidoglycan type | m-DAP Ala Glu |

The bacteriological characteristics of the strains PG-154, PG-186 and PG-303 W are described below.

| Properties | Strains | | |
|---|---|---|---|
| | PG-154 | PG 186 | PG-303W |
| Origin | pit intestinum jejunum | pig colon | pit intestinum duodenum |
| Shape of cells | Coccus (0.8–1.0 × 0.8–1.0)μ | Coccus (0.8–1.0 × 0.8–1.0)μ | Coccus (0.8–1.0 × 0.8–1.0)μ |
| Motility | – | – | – |
| Sporulation | – | – | – |
| Gram stain | + | + | + |
| Oxygen demand | facultative anaerobe | facultative anaerobe | facultative anaerobe |
| Oxidation-fermentation test | fermentative | fermentative | fermentative |
| Fermentation type | homo L-lactic acid | homo L-lactic acid | homo L-lactic acid |
| Catalase | – | – | – |
| Oxidase | – | – | – |
| Nitrogen reduction | – | – | – |
| Gelatin liquefaction | – | – | – |
| Hydrolysis of starch | – | +(weakly) | + |
| Decomposition of escuclin | – | – | + |
| MR test | + | + | + |
| VP test | +(weakly) | +(weakly) | + |
| Formation of indol | – | – | ND |
| $NH_3$ formation from arginine | – | – | – |
| Litmus milk | acid produced (weakly) | acid produced (weakly) | ND |
| Gas formation from glucose | – | – | ND |
| Optimal growth temperature (°C.) | 30–37 | 25–37 | 30–37 |

-continued

| Properties | Strains | | |
|---|---|---|---|
| | PG-154 | PG 186 | PG-303W |
| growth at 45° C. | − | − | − |
| growth at 15° C. | − | − | − |
| growth at pH 4.0 | − | − | ND |
| growth at pH 9.6 | − | − | − |
| Growth in 4% aqueous sodium chloride solution | − | − | − |
| Growth in 6.5% aqueous sodium chloride solution | − | − | − |
| Growth in 40% bile-agar | +(weakly) | +(weakly) | + |
| Mucoid growth (sucrose medium) | − | − | − |
| α-Hemolysis | − | +(weakly) | +(weakly) |
| β-Hemolysis | − | − | − |
| Acid formation | | | |
| adonitol | ND | ND | − |
| arabinose | − | − | − |
| arbutin | +(weakly) | + | + |
| cellobiose | + | + | + |
| fructose | + | + | + |
| galactose | + | + | + |
| Gluconate | − | − | − |
| Glucose | + | + | + |
| Glycerol | − | − | − |
| Inositol | − | − | ND |
| Inulin | − | − | − |
| Lactose | + | + | + |
| Maltose | + | + | + |
| Mannitol | − | − | − |
| Mannose | − | + | + |
| Melezitose | − | − | − |
| Melibiose | − | − | − |
| Raffinose | + | − | + |
| Rhamnose | − | − | − |
| Ribose | − | − | − |
| Salicin | + | + | + |
| Sorbitol | − | − | − |
| Sucrose | + | + | + |
| Trehalose | − | − | + |
| Xylose | − | − | − |
| Xylitol | ND | ND | − |
| GC content (%) of DNA | 40.3 | 40.1 | ND |

In the above Table, Lys, Asp, Ala, Glu, Orn, Ser, and m-DAP represent lysine, aspartic acid, alanine, glutamic acid, ornithne, serine and mesodiaminopimelic acid, respectively. The symbol "ND" means that experiments are not carried out. Consulting Bergey's Manual of Systematic Bacteriology Volume 2 (1986) for a taxonomic classification of the strains based on the above bacteriological characteristics suggested that the UM-12, UM-18 and Rt-5 strains may be adequately relegated to *Lactobacillus reuteri*, although they showed slight differences from the literature characteristics: the UM-18 and Rt-5 strains were negative in the production of acid from arabinose, fructose and ribose (However, Rt-5 was weakly positive in acid production from riboses). Incidentally, since UM-12 and Rt-5 are different from each other only in growth temperature and auxotrophy, they are considered to be mutual variants. The characteristics of the PG-98 strain are substantially identical with those of *Lactobacillus ruminis*. Further, it is appropriate that PG-154 strain, though α-hemolysis is negative, is that of *Streptococcus mitior*; PG-186 strain, though hydrolysis of esculin is negative, is that of *Streptococcus bovis* and PG-303W strain is that of *Streptococcus salivarius*.

The cultivation of these bacterial strains for the accumulation of acid urease can be conducted by the usual procedure of stationary culture, shake culture, submerged aerobic culture or solid culture, either continuously or on an intermittent basis. Particularly preferred is stationary culture. The culture medium may be a usual growth medium for microorganisms. As carbon sources, one or more substances can be used which the strain to be grown may assimilate and can be selected from among various carbohydrates, oils and fats, fatty acids, organic acids, alcohols and so on. As nitrogen sources, there may be employed organic nitrogenous materials such as peptone, soybean flour, cottonseed flour, corn steep liquor, yeast extract, meat extract, malt extract, whey, etc. and inorganic nitrogen compounds such as ammonium sulfate, ammonium chloride, ammonium nitrate, ammonium phosphate, etc. These sources may be used alone or in combination as required. In addition to such carbon and nitrogen sources, the medium preferably contains essential factors and promoters, such as minerals, amino acids, vitamins, etc., for growth and enzyme induction. In addition, there may be added urea and thiourea for induction of acid urease in some instances. For control of pH and foaming during culture, the addition of caustic alkali solution, sodium carbonate solution, or a calcium salt may prove advantageous.

As the incubation temperature, a temperature suited for growth of the strain used can be selected. Usually, the culture can be successfully conducted at 15° to 55° C. and preferably at 25° to 45° C. The incubation time should be sufficient for growth of the organism and production of acid urease and generally ranges from 5 to 120 hours.

After cultivation under the above conditions, the acid urease is generally found to occur in the microbial cells. Therefore, the live cells collected from the broth by centrifugation, sedimentation, flocculation or filtration through a porous, polymeric or ceramic membrane are subjected to any or a combination of freezing-thawing treatment, homogenizer treatment, ultrasonic disruption, osmotic pressure treatment, cell wall membrane lysis, surfactant treatment, etc. The enzyme thus solubilized is then subjected to a suitable combination of the usual enzyme purification procedures such as protamine treatment, fractional precipitation, organic solvent treatment, isoelectric focussing, electrophoresis, ion exchange chromatography, gel filtration, affinity chromatography, crystallization and so on to give an enzyme product which is homogenous as a protein.

METHOD FOR ASSAY OF THE ENZYME ACTIVITY

The urease activity values mentioned in this specification were determined by the following procedure at 37° C. and pH 4.0. Two milliliters of an appropriate dilution of the enzyme solution was incubated at 37° C. for exactly 5 minutes. To this enzyme dilution was added 2 ml of the substrate solution pre-warmed to 37° C. The mixture was shaken and the reaction was conducted at 37° C. for exactly 30 minutes. After the reaction, 4 ml of 10% trichloroacetic acid was immediately added and the mxiture was centrifuged (8,000 rpm, 5 min.). The supernatant (2 ml) was taken and made up with water to 20 ml. To a 4 ml portion of the solution was added 2 ml of color reagent A solution, followed by gentle mixing. Then, 2 ml of color reagent B solution was added, followed by gentle mixing again, and the reaction was conducted at 37° C. for 30 minutes. Then, at room temperature, the absorbance at 640 nm was determined using water as a control.

On the other hand, 2 ml of the above enzyme dilution was shaken with 2 ml of 0.2M citrate buffer in lieu of the substrate solution and the reaction was conducted at 37° C. for exactly 30 minutes. The resulting reaction mixture was subjected to the same procedure as above for an enzyme blank test.

In addition, 2 ml of standard ammonium sulfate solution (50 μg/ml), 1 ml of 10% trichloroacetic acid and 0.5 ml of 0.2M citrate buffer were taken and diluted to 20 ml with water and the resulting solution was subjected to the same color development procedure as above to give a standard solution. On the other hand, 1 ml of 10% trichloroacetic acid and 0.5 ml of 0.2M citrate buffer were taken and diluted to 20 ml with water and the dilution was subjected to the same color development procedure for a standard blank test.

The enzyme activity was calculated by means of the following equation.

Enzyme activity (U/mg) =

$$\frac{OD \text{ of enzyme solution} - OD \text{ of enzyme blank}}{OD \text{ of standard solution} - OD \text{ of standard blank}} \times$$

$$0.76 \times 4 \times \frac{\text{Dilution factor}}{\text{Amount of enzyme (mg)}} \times \frac{1}{30}$$

The amount of enzyme which produces 1 μmole of $NH_3$ per minute is assumed to be unity (1 U). The reagents and test solutions used in the above determination procedures were prepared as follows. The substrate solution was prepared by dissolving 1.0 g of urea in 0.2M citrate buffer to make 100 ml. The 10% trichloroacetic acid solution was prepared by dissolving 10 g of trichloroacetic acid in water to make 100 ml. The color reagent A solution (phenol-nitroprusside sodium solution) was prepared by dissolving 5 g of phenol and 25 mg of nitroprusside sodium in water to make 500 ml. The color reagent B solution (alkaline sodium hypochlorite solution) was prepared by dissolving 5.0 g of sodium hydroxide and 7.5 ml of sodium hypochlorite solution (effective chlorine concentration 5%) in water to make 500 ml. The 0.2M citrate buffer was prepared by dissolving 25.18 g of citric acid (monohydrate) and 23.59 g of sodium citrate (dihydrate) in water to make 1,000 ml (pH 4.0). The standard ammonium sulfate solution (50 pg/ml) was prepared by weighing exactly 250.0 mg of ammonium sulfate, dissolving it in water to make 250 ml, and diluting 5 ml of the solution with water to make 100 ml.

Unlike the conventional urease, the novel urease according to this invention has an optimal pH for activity in the acidic region. Moreover, it is superior to the conventional urease in pH stability, temperature stability and alcohol stability. Therefore, the urease of this invention is a commercially more useful enzyme. Particularly, this urease has a specific activity in excess of 20 U/mg protein and, therefore, is active enough, in a reduced amount, to decompose and eliminate urea from alcoholic liquors (Japanese Patent Application No. 179738/1987), thus being of use for purposes of improving the quality of such products. On the other hand, this urease is very effective as a reagent for the assay of urea in blood and urine samples in clinical laboratory examination or in alcoholic liquors (Japanese Patent Application No. 171751/1987) and other applications. The assay of urea in sake, for instance, can be carried out with high precision by decomposing the urea into ammonia with this enzyme and applying the indophenol method.

BRIEF DESCRIPTION OF THE DRAWINGS

FIGS. 1, 2, 3 and 4 show the relationships of pH and temperature with enzymatic activity of the urease according to Example 1.

In FIG. 1, which shows a pH-activity curve determined at 37° C., ●, ○ and x represent the results of determination in 0.1M citrate buffer, 0.1M acetate buffer, and 0.1M veronal-acetic acid-HCl buffer, respectively.

FIG. 2, which shows the pH stability of the enzyme, indicates the residual activities after 30 minutes at 37° C.

FIG. 3 shows the temperature-activity curve in pH 4, 0.1M citrate buffer.

FIG. 4, which shows the temperature stability of the enzyme, indicates the residual activities after 30 minutes at various temperatures; o represents pH 4 and pH 6 in 0.1M citrate buffer.

FIGS. 5 to 8, FIGS. 9 to 12, FIGS. 13 to 16, FIGS. 17 to 20, FIGS. 21 to 24, FIGS. 25 to 29 and FIGS. 29 to 32 show the relationships of pH and temperature with enzymatic activity of the urease according to Example 2, 3, 4, 5, 6, 7 and 8, respectively. The experiments of FIGS. 5 to 32 was carried out by using 0.1M citrate buffer except the tests of pH stability.

Figures 3, 4:
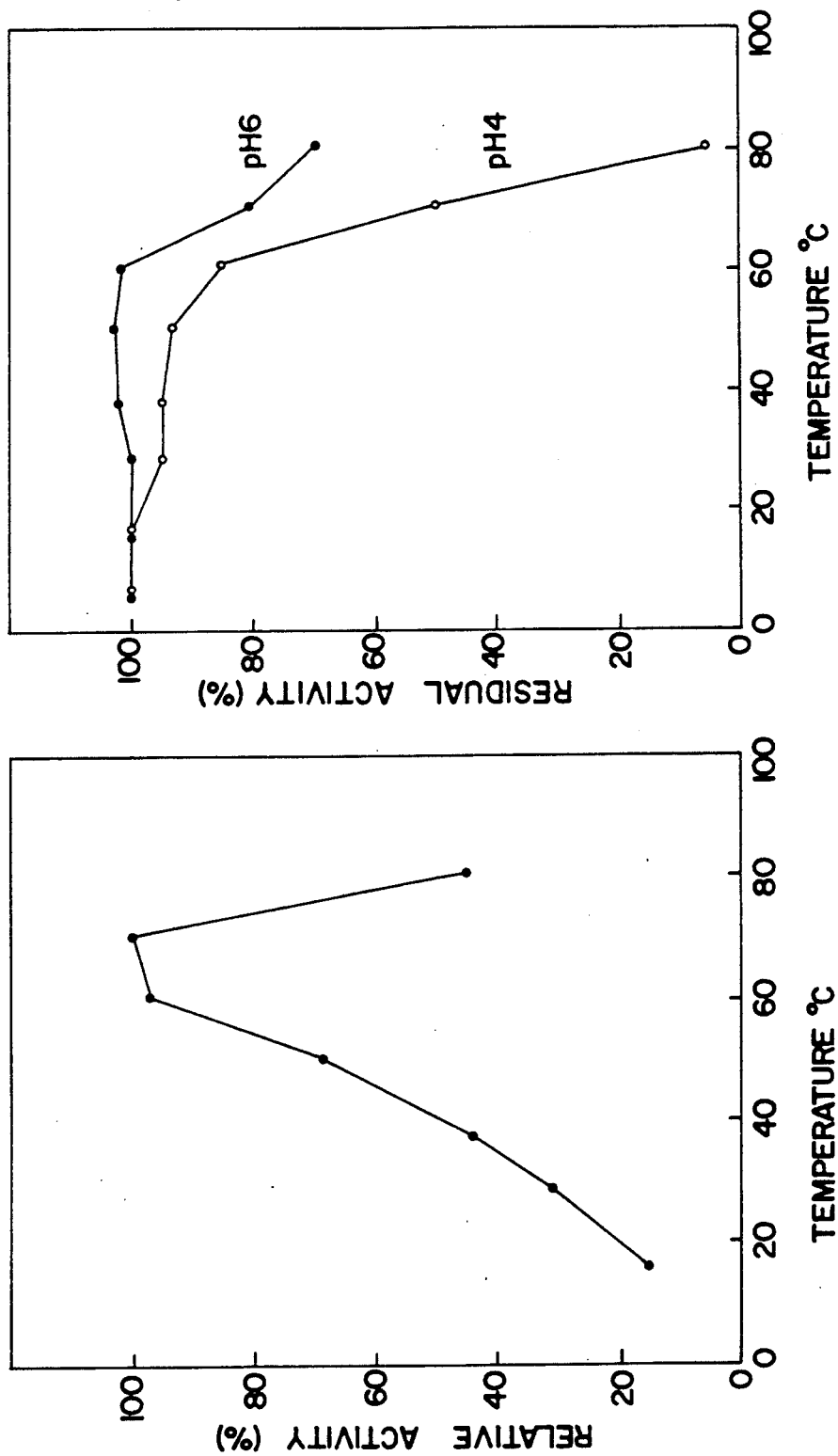

The following examples are intended to illustrate the invention in further detail and should by no means be construed as limiting the scope of the invention.

EXAMPLE 1

*Lactobacillus reuteri* Rt-5 (IFO 14631, FERM BP-1447) grown in a commerical GAM semi-fluid medium (Nissui Seiyaku Co. Ltd., Japan) was inoculated into 10 conical flasks (200 ml capacity) each containing 50 ml of a sterilized seed culture medium composed of 3% glucose, 1.5% polypeptone, 1% meat extract, 0.8% yeast extract, 0.5% sodium chloride, 0.2% anhydrous sodium acetate, 0.005% manganese sulfate (about 4 $H_2O$) and 0.001% nickel sulfate (6 $H_2O$) (pH 7.0, neutralized with 30% NaOH). The flasks were incubated under stationary conditions at 34° C. for 24 hours. The seed cultures thus prepared were transferred to 10 conical flasks (2 l capacity) each containing 1 l of a sterilized medium of the same composition as above and incubation was carried out under stationary conditions at 32° C. for 2 days. The procedure gave 10 l of a culture broth showing 21.6 U/ml of acid urease activity.

The above culture broth was centrifuged to recover the cells, which were washed with 0.05M phosphate buffer (pH 7.2) twice and suspended in 4 l of a solution containing 0.05M phosphate buffer (pH 7.2), 1 mM EDTA and 1 mM dithiothreitol. After addition of 2 l of glass beads ranging from 0.1 to 0.2 mm in diameter, the cell suspension was mechanically disrupted at 4,500 rpm for 20 minutes. The disrupted cell suspension was centrifuged and ethanol was added to the supernatant at a final concentration of 80%. The sediment was collected by centrifugation and dissolved in 0.05M tris-HCl buffer (pH 7.0) containing 1 mM of EDTA and 2-mercaptoethanol. The solution was applied to a Sephadex G-100 column (7.5 cm dia. ×90 cm long) for adsorption and elution was carried out with the same buffer solution. The active fractions were pooled. This eluate was applied to a Sephadex G-200 column (4.5 cm dia. ×150 cm long) equilibrated with the same buffer for adsorption and elution was carried out with the same buffer. The active fractions were pooled and further applied to a DEAE-Sephadex CL-6B column for adsorption, elution being carried out by the gradient elution method using the same buffer solution containing 0 to 0.7M sodium chloride. The active fractions were pooled. This solution was concentrated in an ultrafilter with an Amicon 8200 UK-50 membrane (cut-off molecular weight 50,000). The buffer was changed to 0.005M phosphate buffer (pH 7.0) containing 1 mM 2-mercaptoethanol. Then, the solution was applied to an affinity gel chromatographic column (4 cm dia. ×50 cm long) prepared using Affiprep 10 (the product of Bio-Rad) and hydroxyurea for adsorption, and gradient elution was carried out using 0.005M–0.044M phosphate buffer. The active fractions were pooled and concentrated using the same ultrafilter as mentioned above, followed by fractional precipitation and lyophilization to give 104 mg of purified enzyme powder. This powder had a specific activity of 336.5 U/mg protein and showed a single protein band in polyacrylamide gel electrophoresis. The course of purification is shown in Table 1.

TABLE 1

| Purification steps | Total protein | Total activity ($\times 10^3$ U) | Specific activity (U/mg protein) | Yield (%) |
|---|---|---|---|---|
| Cell-free extract | 14.1 | 183.3 | 13.0 | 100.0 |
| Ethanol | 5.2 | 157.6 | 30.3 | 86.0 |
| Sephadex G-100 | 3.0 | 140.1 | 46.7 | 76.4 |
| Sephadex G-200 | 1.0 | 78.7 | 78.7 | 42.9 |
| DEAE-Sepharose CL-6B | 0.37 | 60.7 | 164.0 | 33.1 |
| Affinity gel | 0.10 | 35.4 | 354.0 | 19.3 |
| Lyophilizate | 0.10 | 35.0 | 336.5 | 19.1 |

The enzymochemical and physiochemical properties of the lyophilized acid enzyme obtained by the above method are shown below.

Acid urease A (1) Action

The enzyme produces 2 moles of ammonia and 1 mole of carbon dioxide gas from 1 mole of urea and 1 mole of water.

(2) Substrate specificity

The enzyme acts most potently on urea and to some extent on ethylurea, biuret, methylurea, allantoic acid and allantoin (Table 2).

TABLE 2

| Substrate | Relative activity (%) |
|---|---|
| Urea | 100.0 |
| Allantoin | 1.2 |
| Allantoic acid | 8.8 |
| Biuret | 64.1 |
| Methylurea | 4.9 |
| Ethylurea | 41.1 |

(3) Optimal pH and pH stability

As shown in FIG. 1, the optimal pH of the enzyme is 2 to 4.5. FIG. 2 shows the residual activities after the enzyme has been allowed to stand at 37° C. and various pH levels for 30 minutes. As apparent from FIG. 2, the enzyme is stable at pH 6–8 and fairly stable in the range of pH 2–10.

(4) Optimal temperature and temperature stability

As shown in FIG. 3, the optimal temperature of the enzyme is 60°–70° C. FIG. 4 shows the residual activities after the enzyme has been allowed to stand at pH 4 and pH 6 and at varing temperatures for 30 minutes. As apparent from FIG. 4, the enzyme is stable at pH 6 up to 60° C. and fairly stable at pH 4 up to 60° C.

(5) Inhibitors

As shown in Table 3, the enzyme is inhibited by mercuric chloride, silver nitrate, iodoacetic acid and acetohydroxamic acid.

TABLE 3

| Inhibitor | Concentration | Relative activity (%) |
|---|---|---|
| None | — | 100.0 |
| $AgNO_3$ | 0.05 mM | 0.7 |
| $HgCl_2$ | 0.05 mM | 0.6 |
| Iodoacetic acid | 1 mM | 15.4 |
| Acetohydroxamic acid | 10 mM | 10.0 |

(6) Molecular weight

As determined by Sephadex G-200 gel filtration, the enzyme has a molecular weight of about 220,000.

(7) Isoelectric point

As determined by isoelectric focussing on polyacrylamide gel, the enzyme shows an isoelectric point of about 4.7.

(8) Crystal structure

This enzyme can hardly be crystallized.

(9) Elemental analysis

Not determined because of the difficulty to crystallize.

(10) Km

The Km value of this enzyme is 1.7 mM (pH 4, 0.1M citrate buffer).

EXAMPLE 2

A seed culture of Lactobacillus fermentum JCM 5867 (IFO 14511, FERM BP-1454) obtained in the same manner as Example 1 was inoculated into 10 conical flasks (2 l capacity) each containing 1 l of a sterilized medium composed of 4% glucose, 1.5% polypeptone, 1% meat extract, 0.8% yeast extract, 0.5% sodium chloride, 0.2% anhydrous sodium acetate, 0.5% urea, 0.05% manganese sulfate (about 4 $H_2O$), 0.002% nickel sulfate (6 $H_2O$), 0.002% cobalt sulfate (7 $H_2O$), 0.005% stannous sulfate and 0.001% strontium sulfate (pH 7.0, adjusted with 30% NaOH) and stationary culture was conducted at 32° C. for 2 days. The procedure gave 10 l of a culture broth showing 5.6 U/ml of acid urease activity.

The cells were collected by centrifuging the above broth, washed with 0.05M phosphate buffer (pH 7.2) twice and suspended in 4 l of a solution containing 0.05M phosphate buffer (pH 7.2), 1 mM EDTA and 1 mM dithiothreitol. After addition of 2 l of glass beads ranging from 0.1 to 0.2 mm in diameter, the cell suspension was mechanically disrupted at 4,500 rpm for 20 minutes. The disrupted cell suspension was centrifuged and ethanol was added to the supernatant at a final concentration of 80%. The sediment was collected by centrifugation and dissolved in 0.05M Tris-HCl buffer (pH 7.0) containing 1 mM of EDTA and 2-mercaptoethanol. The solution was applied to a Sephadex G-100 column (7.5 cm dia.×90 cm long) for adsorption and elution was carried out with the same buffer. The active fractions were pooled and applied to a Sephadex G-200 column (4.5 cm dia. ×150 cm) for adsorption and elution was carried out with the same buffer. The active fractions were pooled and further applied to a DEAE-Sephadex A-50 column equilibrated with the same buffer, gradient elution being carried out with the same buffer containing 0–0.7M NaCl. The active fractions were pooled. The specific activity of this solution was 35.2 U/mg protein and the yield of activity was 43.7%. The enzymochemical properties of this product were as follows.

Acid urease B (1) Action

The enzyme produces 2 moles of ammonia and 1 mole of carbon dioxide gas from 1 mole of urea and 1 mole of water.

(2) Substrate specificity

The enzyme acts most potently on urea and to some extent on ethylurea, biuret, methylurea and allantoic acid (Table 4).

TABLE 4

| Substrate | Relative activity (%) |
| --- | --- |
| Urea | 100.0 |
| Allantoin | 0.0 |
| Allantoic acid | 3.7 |
| Biuret | 72.0 |
| Methylurea | 14.0 |

TABLE 4-continued

| Substrate | Relative activity (%) |
| --- | --- |
| Ethylurea | 46.0 |

(3) Optimal pH and pH stability

Figure 6:
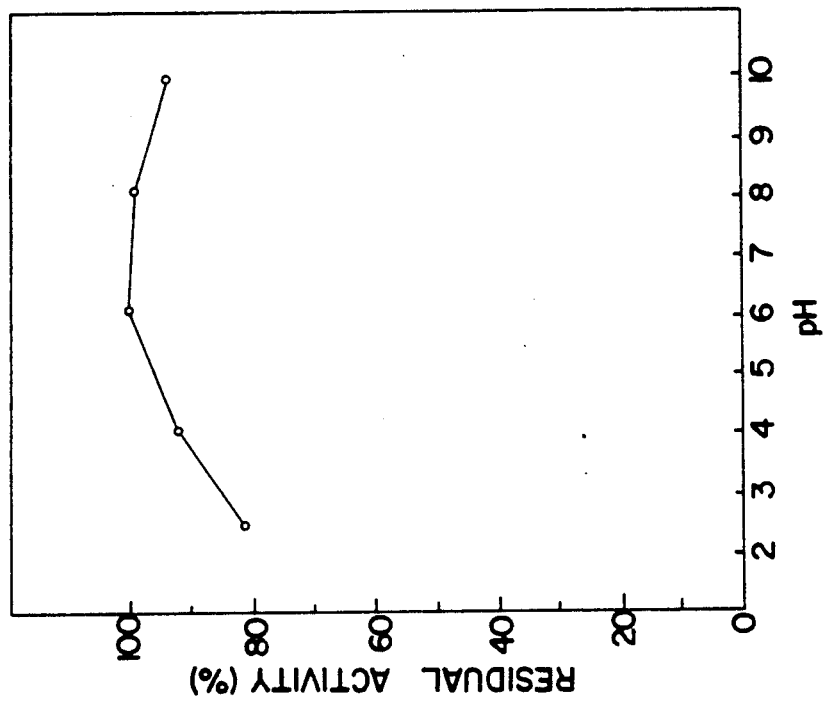
Figure 5:
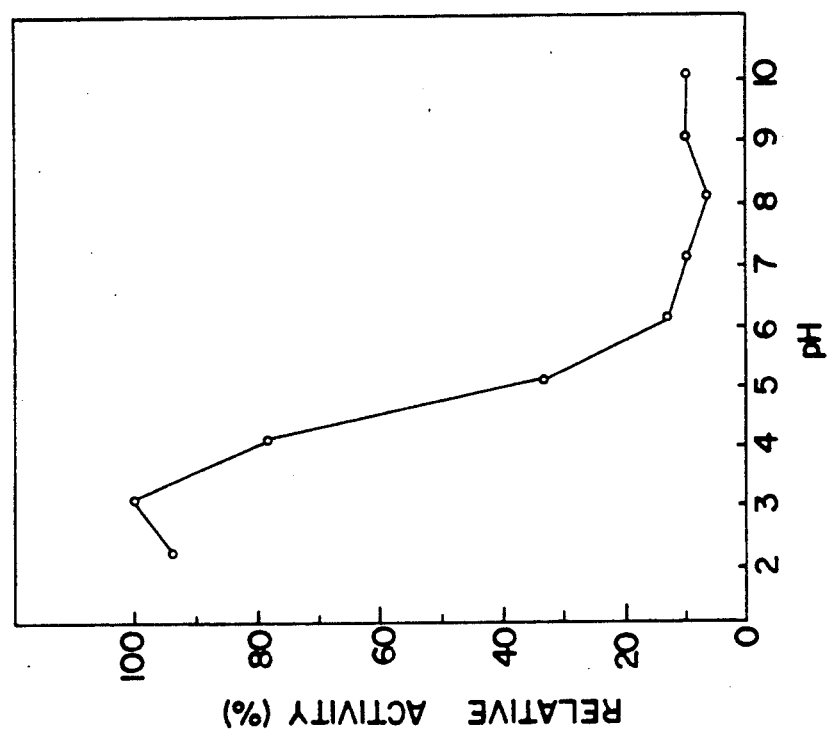

As shown in FIG. 5, the optimal pH was about pH 3. FIG. 6 shows the residual activities after the enzyme has been allowed to stand at 37° C. and varying pH for 30 minutes. As apparent from FIG. 6, the enzyme is stable at pH 6–8.

(4) Optimal temperature and temperature stability

As shown in FIG. 7, the optimal temperature of this enzyme is 60°–70° C. FIG. 8 shows the residual activities after the enzyme has been allowed to stand at pH 4 and 6 for 30 minutes. As apparent from FIG. 8, the enzyme is stable at pH 6 up to 80° C. and at pH 4 up to 60° C.

(5) Inhibitors

As shown in Table 5, the enzyme is inhibited by mercuric chloride, silver nitrate, copper sulfate, iodoacetic acid and acetohydroxamic acid.

TABLE 5

| Inhibitor | Concentration | Relative activity (%) |
| --- | --- | --- |
| None | | 100.0 |
| $AgNO_3$ | 0.05 mM | 0.4 |
| $CuSO_4.5H_2O$ | 0.4 mM | 47.6 |
| $HgCl_2$ | 0.005 mM | 0.8 |
| Iodoacetic acid | 1 mM | 14.9 |
| Acetohydroxamic acid | 10 mM | 16.0 |

(6) Molecular weight

As determined by Sephadex G-200 gel filtration, this enzyme has a molecular weight of about 210,000 to 220,000.

(7) Isoelectric point

As determined by isoelectric focussing on polyacrylamide gel, the enzyme shows an isoelectric point of about 4.8.

(8) Crystal structure

This enzyme can hardly be crystallized.

(9) Elemental analysis

Not determined because of the difficulty to crystallize.

(10) Km

The Km value of this enzyme is 1.0 mM (pH 2, 0.1M citrate buffer).

EXAMPLE 3

*Streptococcus bovis* PG-186 (IFO 14634, FERM BP-1449) grown in a commercial GAM semi-fluid medium (Nissui Seiyaku) was inoculated into 10 conical flasks (200 ml capacity) each containing 50 ml of a sterilized seed culture medium composed of 4% glucose, 1.5% polypeptone, 1% meat extract, 0.8% yeast extract, 0.5% sodium chloride, 0.2% anhydrous sodium acetate, 0.5% urea, 0.005% manganese sulfate (about 4 $H_2O$) and 0.001% nickel sulfate (6 $H_2O$) (pH 7.0, neutralized with 30% NaOH). The flasks were incubated under stationary conditions at 34° C. for 24 hours. The seed cultures thus prepared were transferred to 10 conical flasks (2 l capacity) each containing 1 l of a sterilized medium of the same composition as above and incubation was carried out under stationary conditions at 32° C. for 2 days. The procedure gave 10 l of a culture broth showing 7.6 U/ml of acid urease activity.

The above culture broth was centrifuged to recover the cells, which were washed with 0.05M phosphate buffer (pH 7.2) twice and suspended in 4 l of a solution containing 0.05M phosphate buffer (pH 7.2), 1 mM EDTA and 1 mM dithiothreitol. After addition of 2 l of glass beads ranging from 0.1 to 0.2 mm in diameter, the cell suspension was mechanically disrupted at 4,500 rpm for 20 minutes. The disrupted cell suspension was centrifuged and ethanol was added to the supernatant at a final concentration of 80%. The sediment was collected by centrifugation and dissolved in 0.05M tris-HCl buffer (pH 7.0) containing 1 mM of EDTA and 2-mercaptoethanol. The solution was applied to a Sephadex G-100 column (7.5 cm dia.×90 cm long) for adsorption and elution was carried out with the same buffer solution. The active fractions were pooled. This eluate was applied to a Sephadex G-200 column (4.5 cm dia.×150 cm long) equilibrated with the same buffer for adsorption and elution was carried out with the same buffer. The active fractions were pooled and further applied to a DEAE-Sephadex CL-6B column for adsorption, elution being carried out by the gradient elution method using the same buffer solution containing 0 to 0.7M sodium chloride. The active fractions were pooled. This solution was concentrated in a ultrafilter with an Amicon 8200 UK-50 membrane (cut-off molecular weight 50,000). The buffer was changed to 0.005M phosphate buffer (pH 7.0) containing 1 mM 2-mercaptoethanol. Then, the solution was applied to an affinity gel chromatographic column (4 cm dia.×50 cm long) prepared using Affiprep 10 (the product of Bio-Rad) and hydroxyurea for adsorption, and gradient elution was carried out using 0.005M–0.044M phosphate buffer. The active fractions were pooled and concentrated using the same ultrafilter as mentioned above, followed by fractional precipitation and lyophilization to give 104 mg of purified enzyme powder. This powder had a specific activity of 124 U/mg protein.

The enzymochemical and physicochemical properties of the lyophilized acid enzyme obtained by the above method are shown below.

Acid urease C (1) Action

The enzyme produces 2 moles of ammonia and 1 mole of carbon dioxide gas from 1 mole of urea and 1 mole of water.

(2) Substrate specificity

The enzyme acts most potently on urea (Table 6).

TABLE 6

| Substrate | Relative activity (%) |
| --- | --- |
| Urea | 100.0 |
| Allantoic acid | 0.0 |
| Biuret | 0.0 |
| Ethylurea | 0.0 |

(3) Optimal pH and pH stability

Figure 10:
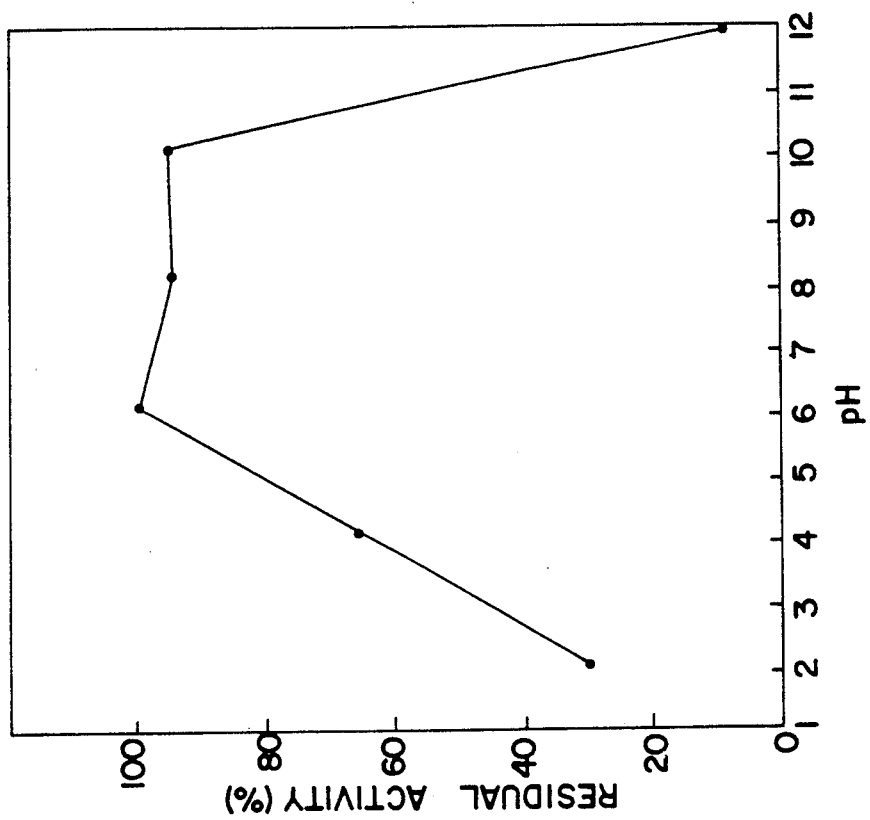
Figure 9:
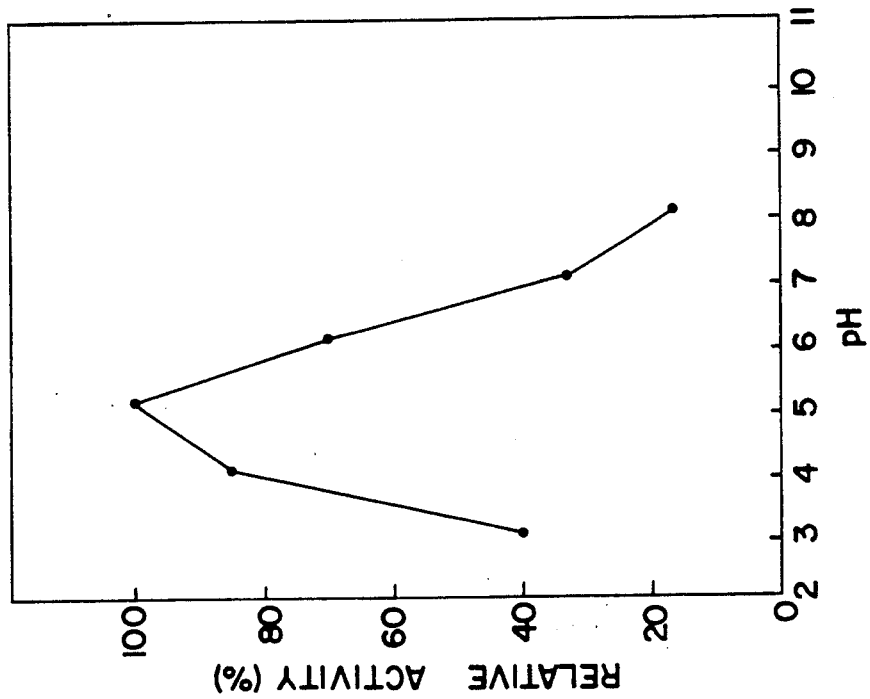

As shown in FIG. 9, the optimal pH of the enzyme is about 5. FIG. 10 shows the residual activities after the enzyme has been allowed to stand at 37° C. and various pH levels for 30 minutes. As apparent from FIG. 10, the enzyme is stable at pH 6–10.

(4) Optimal temperature and temperature stability

Figure 12:
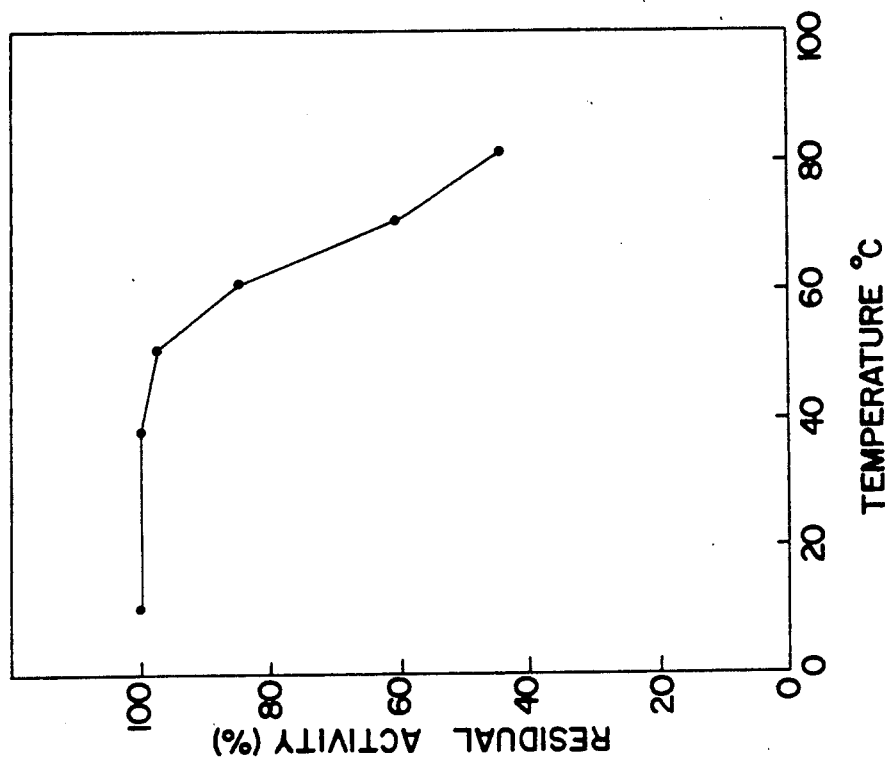
Figure 11:
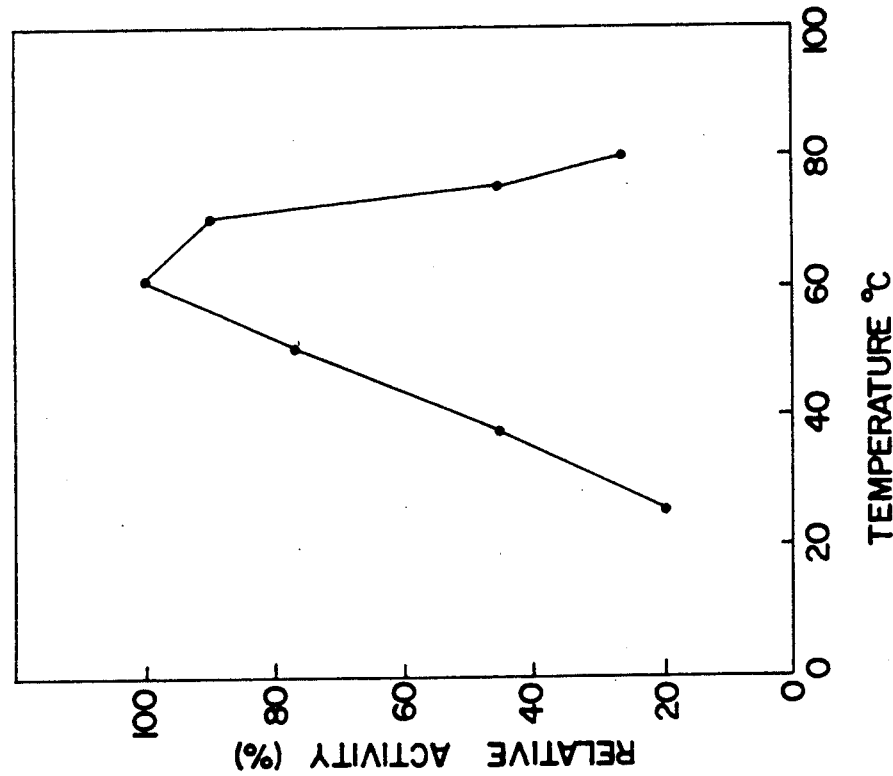

As shown in FIG. 11, the optimal temperature of the enzyme is 60°–70° C. FIG. 12 shows the residual activities after the enzyme has been allowed to stand at pH 6 and at varing temperatures for 30 minutes. As apparent from FIG. 12, the enzyme is stable at pH 6 up to 50° C.

(5) Inhibitors

As shown in Table 7, the enzyme is inhibited by mercuric chloride, and acetohydroxamic acid.

TABLE 7

| Inhibitor | Concentration | Relative activity (%) |
| --- | --- | --- |
| None | | 100.0 |
| $HgCl_2$ | 1 mM | 0.0 |
| Iodoacetic acid | 10 mM | 89.8 |
| Acetohydroxamic acid | 10 mM | 9.8 |

(6) Molecular weight

As determined by polyacryl amide gel electrophoresis [H. Eng et al; Can. J. Microbial., 32, 487 (1986)], the enzyme has a molecular weight of about 190,000.

As determined by Sephadex G-200 gel filtration, the enzyme has a molecular weight of about 170,000.

(7) Isoelectric point

As determined by isoelectric focussing on polyacrylamide gel, the enzyme shows an isoelectric point of about 4.7.

(8) Crystal structure

This enzyme can hardly be crystallized.

(9) Elemental analysis

Not determined because of the difficulty to crystallize.

(10) Km

The Km value of this enzyme is 0.2 mM (pH 5,0, 0.1M citrate buffer).

EXAMPLE 4

Streptococcus mitior PG-154 (IFO 14633, FERM BP-1448) was cultivated in the same manner as Example 3. The procedure gave 10 l of a culture broth showing 5.4 U/ml.

The above culture broth was centrifuged to recover the cells, which were washed with 0.05M phosphate buffer (pH 7.2) twice and suspended in 4 l of a solution containing 0.05M phosphate buffer (pH 7.2), 1 mM EDTA and 1 mM dithiothreitol. After addition of 2 l of glass beads ranging from 0.1 to 0.2 mm in diameter, the cell suspension was mechanically disrupted at 4,500 rpm for 20 minutes. The disrupted cell suspension was centrifuged and ethanol was added to the supernatant at a final concentration of 80%. The sediment was collected by centrifugation and dissolved in 0.05M tris-HCl buffer (pH 7.0) containing 1 mM of EDTA and 2-mercaptoethanol. The solution was applied to a Sephadex G-100 column (7.5 cm dia.×90 cm long) for adsorption and elution was carried out with the same buffer solution. The active fractions were pooled. This eluate was applied to a Sephadex G-200 column (4.5 cm dia.×150 cm long) equilibrated with the same buffer for adsorption and elution was carried out with the same buffer. The active fractions were pooled and further applied to a DEAE-Sephadex CL-6B column for adsorption, elution being carried out by the gradient elution method using the same buffer solution containing 0 to 0.7M sodium chloride. The active fractions were pooled. The specific activity of this solution was 76.3 U/mg protein and the yield of activity was 38.7%. The enzymochemical properties of this product were as follows.

Acid urease D (1) Action

The enzyme produces 2 moles of ammonia and 1 mole of carbon dioxide gas from 1 mole of urea and 1 mole of water.

(2) Substrate specificity

The enzyme acts most potently on urea and to some extent on biuret and ethylurea (Table 8).

TABLE 8

| Substrate | Relative activity (%) |
|---|---|
| Urea | 100.0 |
| Allantoic acid | 0.0 |
| Biuret | 22.0 |
| Ethylurea | 18.8 |

(3) Optimal pH and pH stability

Figure 14:
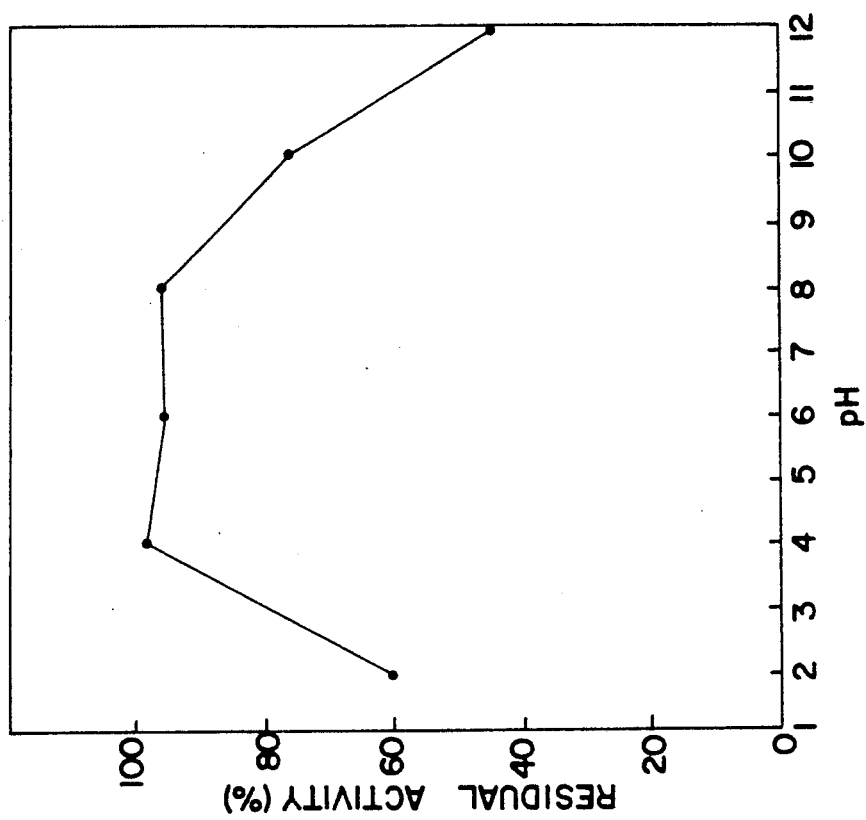
Figure 13:
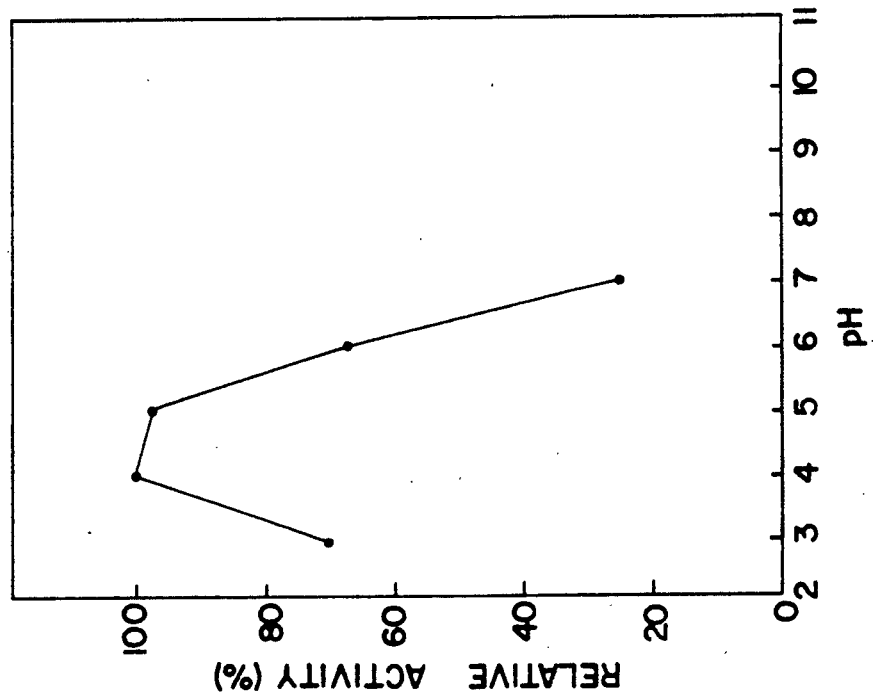

As shown in FIG. 13, the optimal pH of the enzyme is 4 to 5. FIG. 14 shows the residual activities after the enzyme has been allowed to stand at 37° C. and various pH levels for 30 minutes. As apparent from FIG. 14, the enzyme is stable at pH 4-8.

(4) Optimal temperature and temperature stability

Figure 16:
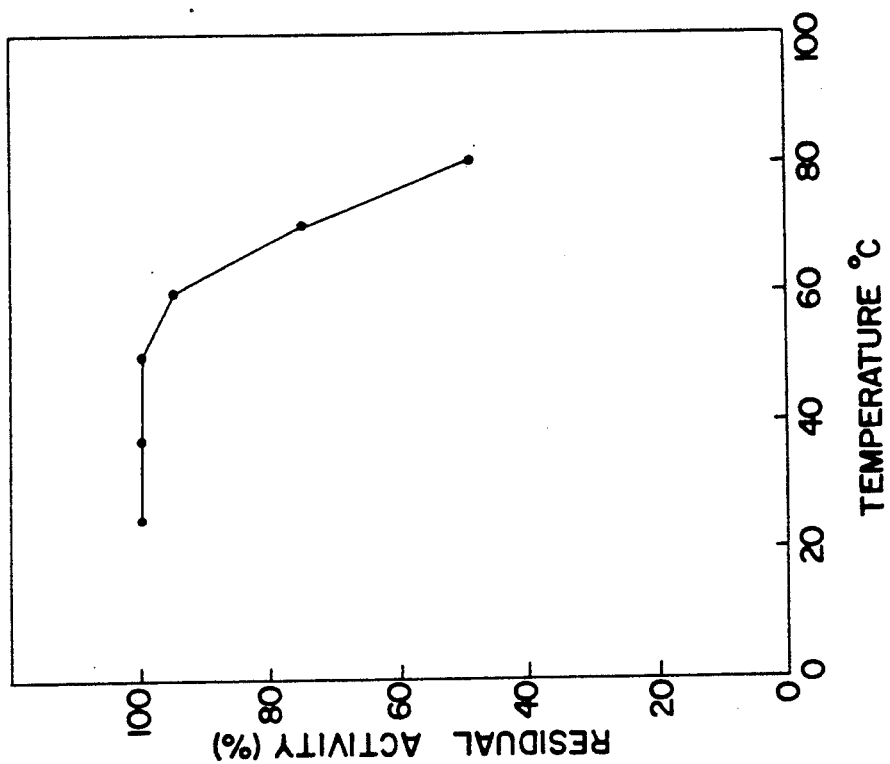
Figure 15:
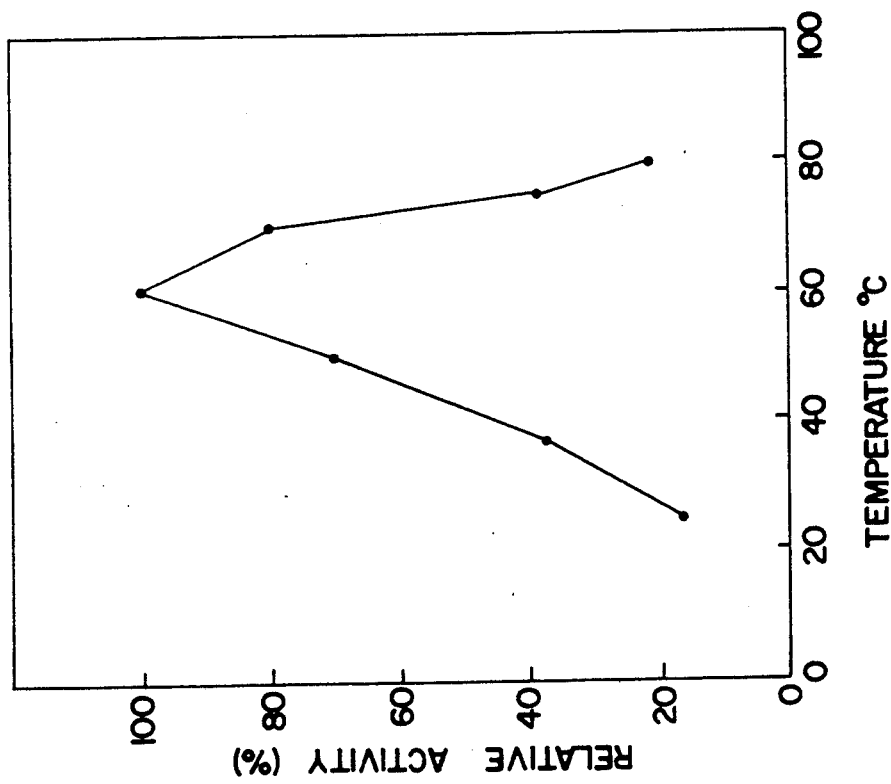

As shown in FIG. 15, the optimal temperature of the enzyme is around 60° C. FIG. 16 shows the residual activities after the enzyme has been allowed to stand at pH 6 for 30 minutes. As apparent from FIG. 16, the enzyme is stable at pH 6 up to 60° C.

(5) Inhibitors

As shown in Table 9, the enzyme is inhibited by mercuric chloride, iodoaclic acid and acetohydroxamic acid.

TABLE 9

| Inhibitor | Concentration | Relative activity (%) |
|---|---|---|
| None | | 100.0 |
| HgCl$_2$ | 1 mM | 0.0 |
| Iodoacetic acid | 10 mM | 0.6 |
| Acetohydroxamic acid | 10 mM | 19.2 |

(6) Molecular weight

As determined by polyacryl amide gel electrophoresis the enzyme has a molecular weight of about 160,000. As determined by Sephadex G-200 gel filtration, the enzyme has a molecular weight of about 170,000.

(7) Isoelectric point

As determined by isoelectric focussing on polyacrylamide gel, the enzyme shows an isoelectric point of about 4.6.

(8) Crystal structure

This enzyme can hardly be crystallized.

(9) Elemental analysis

Not determined because of the difficulty to crystallize.

(10) Km

The Km value of this enzyme is 0.3 mM (pH 4, 0.1M citrate buffer).

EXAMPLE 5

*Streptococcus salivarius* PG-303W (IFO 14746, FERM BP-1856) was cultivated in the same manner as Example 3. The procedure gave 10 l of a culture broth showing 4.3 U/ml. The above culture broth was subjected to the same purification process as Example 4 to give the enzyme having a specific activity of 68.2 U/mg protein. The yield of activity was 41.2%. The enzymochemical properties of this product were as follows.

Acid urease E (1) Action

The enzyme produces 2 moles of ammonia and 1 mole of carbon dioxide gas from 1 mole of urea and 1 mole of water.

(2) Substrate specificity

The enzyme acts most potently on urea and to some extent on biuret and allantoic acid (Table 10).

TABLE 10

| Substrate | Relative activity (%) |
|---|---|
| Urea | 100.0 |
| Allantoic acid | 12.0 |
| Biuret | 60.0 |
| Ethylurea | 50.0 |

(3) Optimal pH and pH stability

As shown in FIG. 17, the optimal pH of the enzyme is 4. FIG. 18 shows the residual activities after the enzyme has been allowed to stand at 37° C. and various pH levels for 30 minutes. As apparent from FIG. 18, the enzyme is stable at pH 6-11.

(4) Optimal temperature and temperature stability

Figure 20:
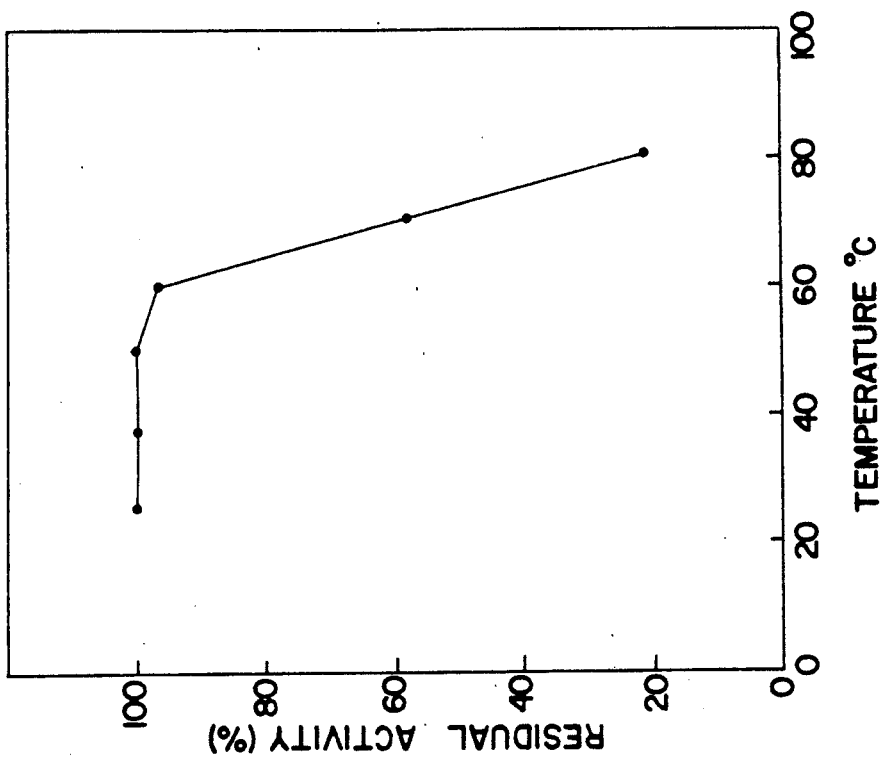
Figure 19:
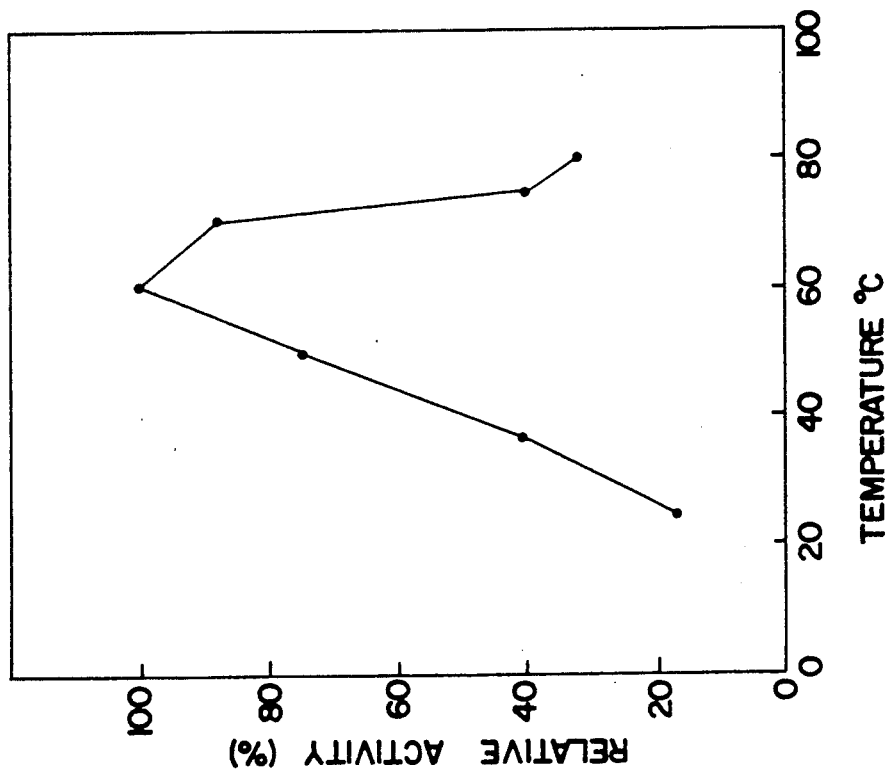

As shown in FIG. 19, the optimal temperature of the enzyme is 60°-70° C. FIG. 20 shows the residual activities after the enzyme has been allowed to stand at pH 6 and at varing temperatures for 30 minutes. As apparent from FIG. 20, the enzyme is stable at pH 6 up to 60° C.

(5) Inhibitors

As shown in Table 11, the enzyme is inhibited by mercuric chloride and acetohydroxamic acid.

TABLE 11

| Inhibitor | Concentration | Relative activity (%) |
|---|---|---|
| None | | 100.0 |
| HgCl$_2$ | 0.05 mM | 2.0 |
| Iodoacetic acid | 10 mM | 100.0 |
| Acetohydroxamic acid | 10 mM | 15.2 |

(6) Molecular weight

As determined by polyacryl amide gel electrophoresis the enzyme has a molecular weight of about 110,000. As determined by Sephadex G-200 gel filtration, the enzyme has a molecular weight of about 140,000.

(7) Isoelectric point

As determined by isoelectric focussing on polyacrylamide gel, the enzyme shows an isoelectric point of about 4.7.

(8) Crystal structure

This enzyme can hardly be crystallized.

(9) Elemental analysis

Not determined because of the difficulty to crystallize.

(10) Km

The Km value of this enzyme is 0.2 mM (pH 4, 0.1M citrate buffer)

EXAMPLE 6

*Lactobacillus ruminis* PG-98 (IFO 14632, FERM BP-1906) was cultivated in the same manner as Example 1. The procedure gave 10 l of a culture broth showing 5.2 U/ml of acid urease activity. The above culture broth was subjected to the same purification process as Example 2 to give the enzyme having a specific activity of 36.7 U/mg protein. The yield of activity was 42.8%. The enzymochemical properties of this product were as follows.

Acid urease F (1) Action

The enzyme produces 2 moles of ammonia and 1 mole of carbon dioxide gas from 1 mole of urea and 1 mole of water.

(2) Substrate specificity

The enzyme acts most potently on urea and to some extent on ethylurea and biuret (Table 12).

TABLE 12

| Substrate | Relative activity (%) |
| --- | --- |
| Urea | 100.0 |
| Allantoic acid | 0.0 |
| Biuret | 26.0 |
| Ethylurea | 5.0 |

(3) Optimal pH and pH stability

Figure 21:
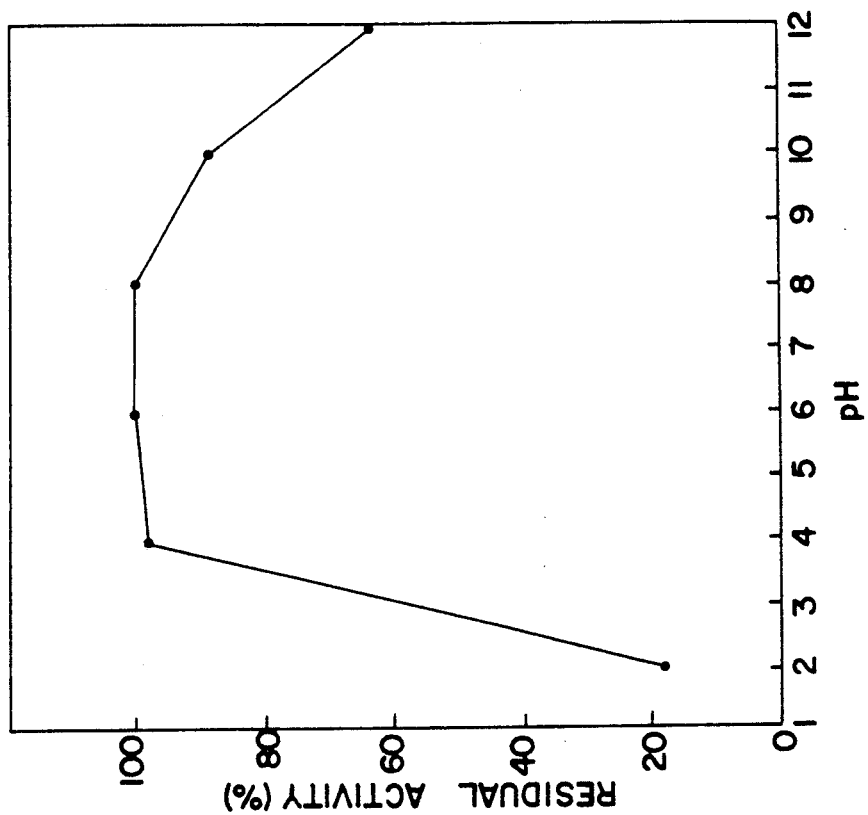
Figure 22:
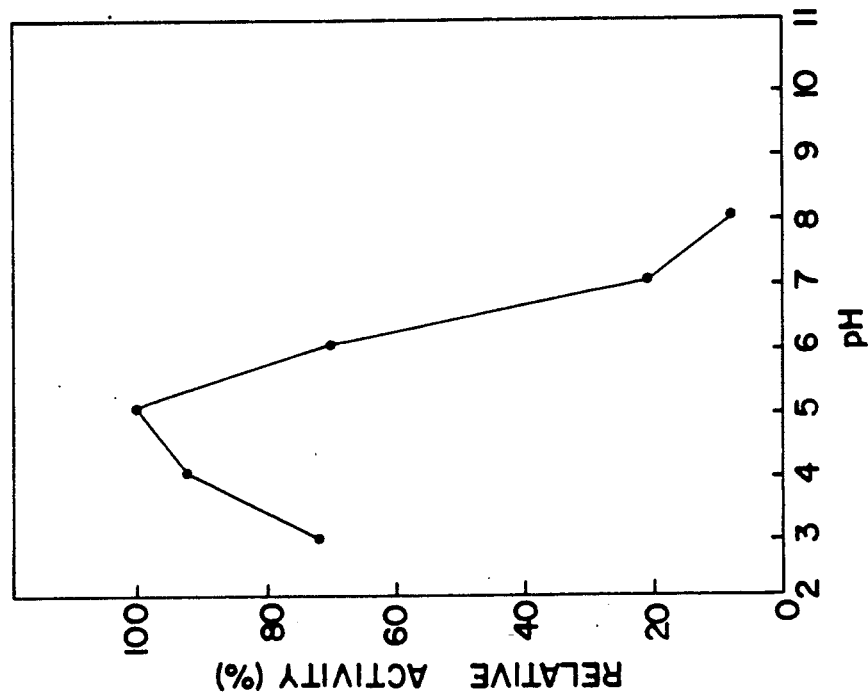

As shown in FIG. 21, the optimal pH of the enzyme is 5. FIG. 22 shows the residual activities after the enzyme has been allowed to stand at 37° C. and various pH levels for 30 minutes. As apparent from FIG. 22, the enzyme is stable at pH 4–8.

(4) Optimal temperature and temperature stability

Figure 24:
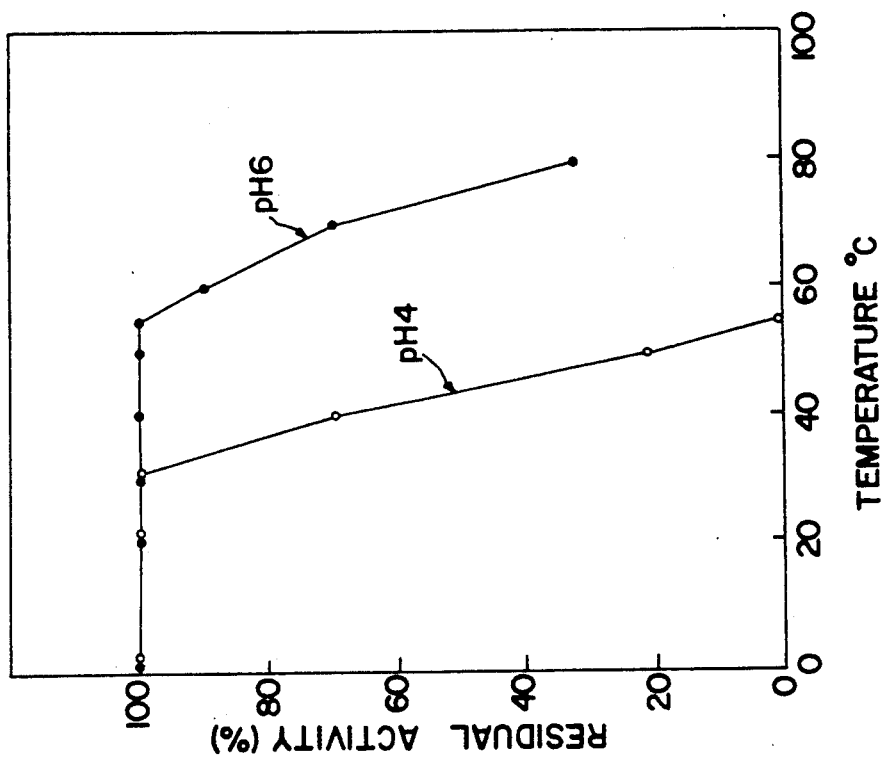
Figure 23:
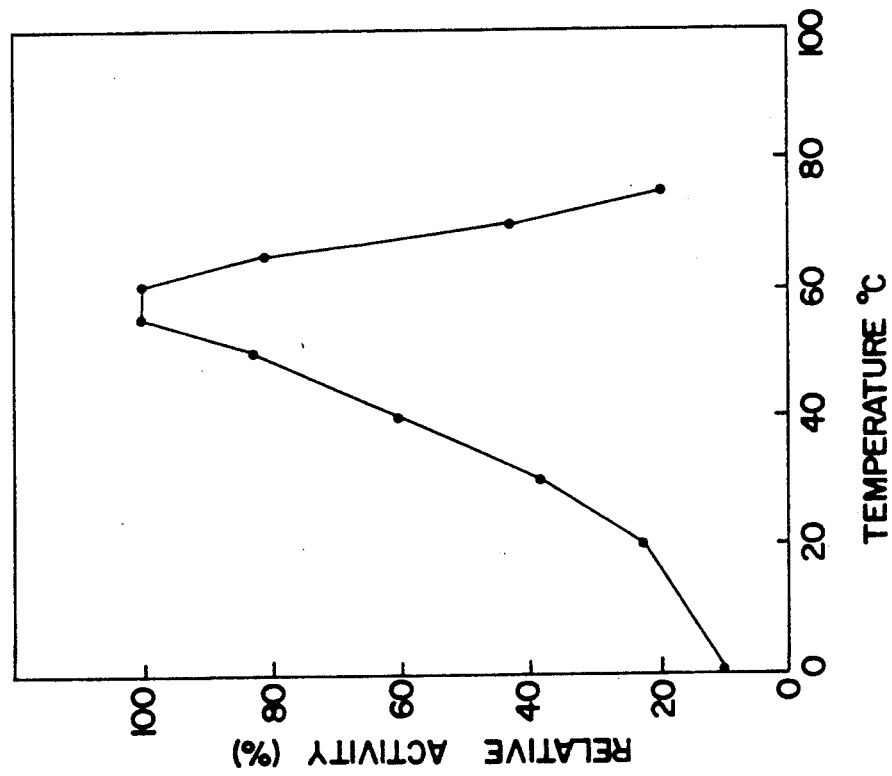

As shown in FIG. 23, the optimal temperature of the enzyme is 55°–60° C. FIG. 24 shows the residual activities after the enzyme has been allowed to stand at pH 6 for 30 minutes. As apparent from FIG. 24, the enzyme is stable at pH 6 up to 55° C. and at pH 4 up to 30° C.

(5) Inhibitors

As shown in Table 3, the enzyme is inhibited by mercuric chloride, iodoacetic acid and acetohydroxamic acid.

TABLE 13

| Inhibitor | Concentration | Relative activity (%) |
| --- | --- | --- |
| None | | 100.0 |
| HgCl$_2$ | 0.05 mM | 0.0 |
| Iodoacetic acid | 10 mM | 50.0 |
| Acetohydroxamic acid | 10 mM | 0.0 |

(6) Molecular weight

As determined by Sephadex G-200 gel filtration, the enzyme has a molecular weight of about 150,000.

(7) Isoelectric point

As determined by isoelectric focussing on polyacrylamide gel, the enzyme shows an isoelectric point of about 4.7.

(8) Crystal structure

This enzyme can hardly be crystallized.

(9) Elemental analysis

Not determined because of the difficulty to crystallize.

(10) Km

The Km value of this enzyme is 1.2 mM (pH 5, 0.1M citrate buffer).

EXAMPLE 7

*Lactobacillus reuteri* UM-12 (IFO 14629, FERM BP-1904) was cultivated in the same manner as Example 1. The procedure gave 10 l of a culture broth showing 3.6 U/ml of acid urease activity. The above culture broth was subjected to the same purification process as Example 2 to give the enzyme having a specific activity of 33.4 U/mg protein. The yield of activity was 45.3%. The enzymochemical properties of this product were as follows.

Acid urease G (1) Action

The enzyme produces 2 moles of ammonia and 1 mole of carbon dioxide gas from 1 mole of urea and 1 mole of water.

(2) Substrate specificity

The enzyme acts most potently on urea and to some extent on ethylurea and biuret (Table 14).

TABLE 14

| Substrate | Relative activity (%) |
| --- | --- |
| Urea | 100.0 |
| Allantoic acid | 0.0 |
| Biuret | 7.9 |
| Ethylurea | 25.5 |

(3) Optimal pH and pH stability

Figure 26:
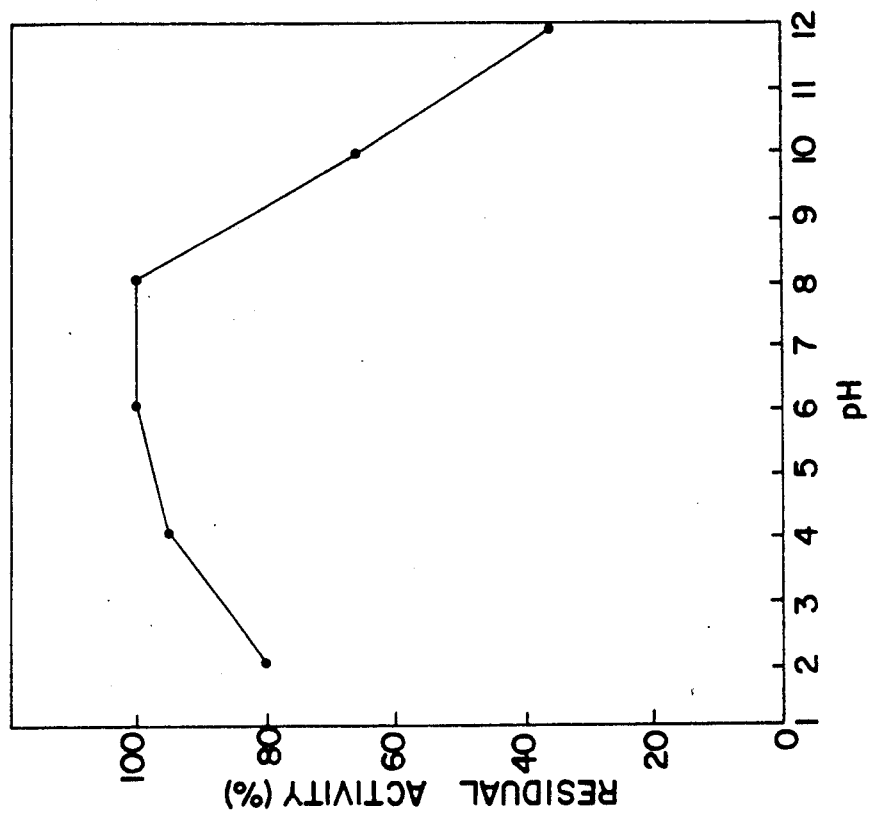
Figure 25:
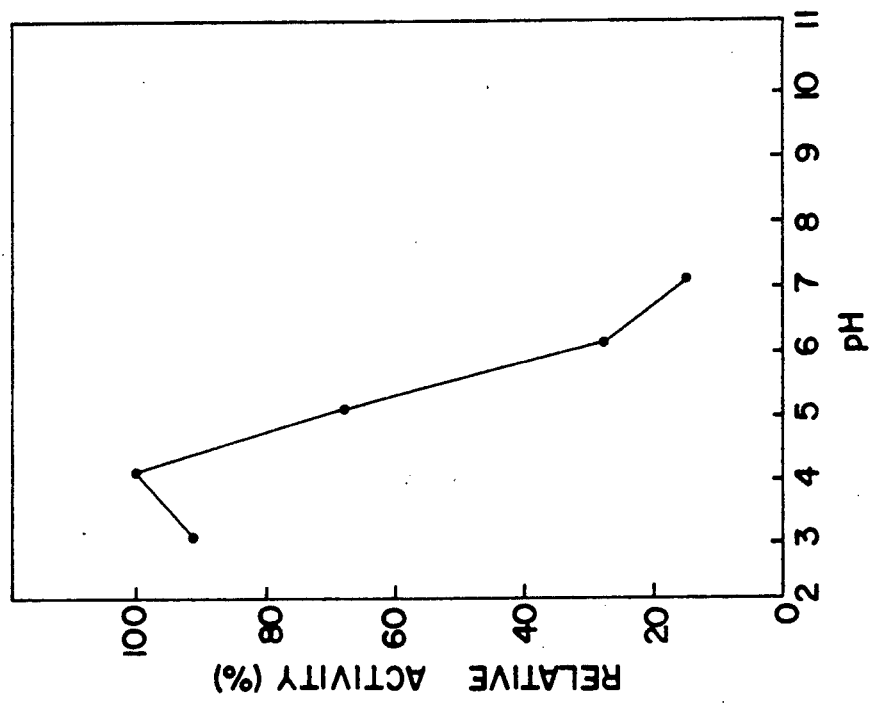

As shown in FIG. 25, the optimal pH of the enzyme is 4. FIG. 26 shows the residual activities after the enzyme has been allowed to stand at 37° C. and various pH levels for 30 minutes. As apparent from FIG. 26, the enzyme is stable at pH 4–8.

(4) Optimal temperature and temperature stability

Figure 28:
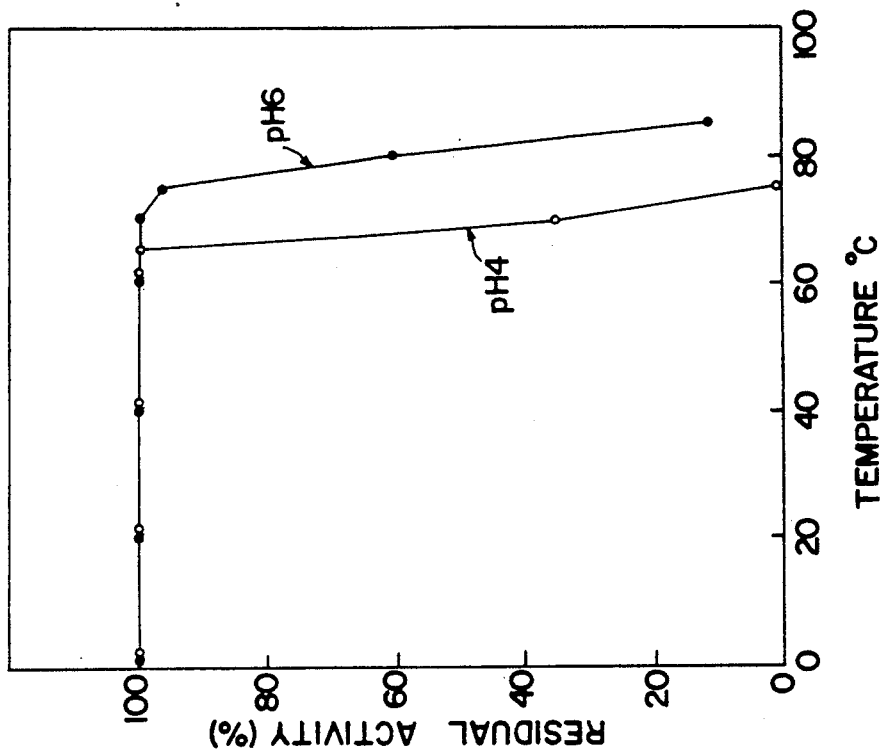
Figure 27:
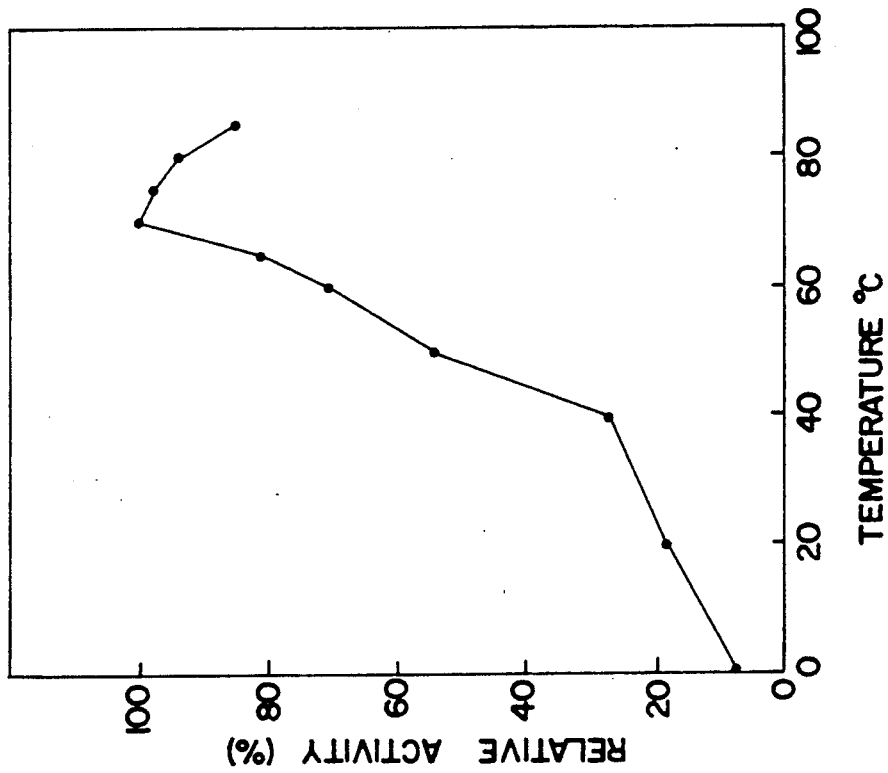

As shown in FIG. 27, the optimal temperature of the enzyme is 70°–75° C. FIG. 28 shows the residual activities after the enzyme has been allowed to stand at pH 4 and pH 6 for 30 minutes. As apparent from FIG. 28, the enzyme is stable at pH 6 up to 75° C. and at pH 4 up to 65° C.

(5) Inhibitors

As shown in Table 15, the enzyme is inhibited by mercuric chloride and acetohydroxamic acid.

TABLE 15

| Inhibitor | Concentration | Relative activity (%) |
| --- | --- | --- |
| None | | 100.0 |
| HgCl$_2$ | 0.05 mM | 0.0 |
| Iodoacetic acid | 10 mM | 100.0 |
| Acetohydroxamic acid | 10 mM | 17.1 |

(6) Molecular weight

As determined by Sephadex G-200 gel filtration, the enzyme has a molecular weight of about 210,000.

(7) Isoelectric point

As determined by isoelectric focussing on polyacrylamide gel, the enzyme shows an isoelectric point of about 4.8.

(8) Crystal structure

This enzyme can hardly be crystallized.

(9) Elemental analysis

Not determined because of the difficulty to crystallize.

(10) Km

The Km value of this enzyme is 1.3 mM (pH 4, 0.1M citrate buffer).

EXAMPLE 8

*Lactobacillus reuteri* UM-18 (IFO 14630, FERM BP-1905) was cultivated in the same manner as Example 1. The procedure gave 10 l of a culture broth showing 4.5 U/ml of acid urease activity. The above culture broth was subjected to the same purification process as Example 2 to give the enzyme having a specific activity of 39.8 U/mg protein. The yield of activity was 41.7%. The enzymochemical properties of this product were as follows.

Acid urease H (1) Action

The enzyme produces 2 moles of ammonia and 1 mole of carbon dioxide gas from 1 mole of urea and 1 mole of water.

(2) Substrate specificity

The enzyme acts most potently on urea and to some extent on ethylurea, biuret and allantoic acid (Table 16).

TABLE 16

| Substrate | Relative activity (%) |
|---|---|
| Urea | 100.0 |
| Allantoic acid | 12.3 |
| Biuret | 82.4 |
| Ethylurea | 66.2 |

(3) Optimal pH and pH stability

As shown in FIG. 29, the optimal pH of the enzyme is 3. FIG. 30 shows the residual activities after the enzyme has been allowed to stand at 37° C. and various pH levels for 30 minutes. As apparent from FIG. 30, the enzyme is stable at pH 5–8.

(4) Optimal temperature and temperature stability

As shown in FIG. 31, the optimal temperature of the enzyme is 70°–75° C. FIG. 32 shows the residual activities after the enzyme has been allowed to stand at pH 4 and pH 6 for 30 minutes. As apparent from FIG. 32, the enzyme is stable at pH 6 up to 70° C. and at pH 4 up to 65° C.

(5) Inhibitors

As shown in Table 17, the enzyme is inhibited by mercuric chloride and acetohydroxamic acid.

TABLE 17

| Inhibitor | Concentration | Relative activity (%) |
|---|---|---|
| None | | 100.0 |
| HgCl$_2$ | 0.05 mM | 0.0 |
| Iodoacetic acid | 10 mM | 99.0 |
| Acetohydroxamic acid | 10 mM | 7.9 |

(6) Molecular weight

As determined by Sephadex G-200 gel filtration, the enzyme has a molecular weight of about 230,000.

(7) Isoelectric point

As determined by isoelectric focussing on polyacrylamide gel, the enzyme shows an isoelectric point of about 4.5.

(8) Crystal structure

This enzyme can hardly be crystallized.

(9) Elemental analysis

Not determined because of the difficulty to crystallize.

(10) Km

The Km value of this enzyme is 4.8 mM (pH 3, 0.1M citrate buffer).

TEST EXAMPLE 1

The enzyme activity of Acid ureases C, D and obtained by Examples 3–5 was assayed by using the reaction solution containing ethanol in various concentrations. As shown in Table 18, these ureases can act on urea even in the presence of 20 or 50% ethanol.

TABLE 18

| Acid urease | Concentration of ethanol (%) | | |
|---|---|---|---|
| | 0 | 20 | 50 |
| Acid urease C | 100 | 84.2 | 51.6 |
| Acid urease D | 100 | 85.0 | 50.4 |
| Acid urease E | 100 | 82.6 | 47.6 |

Relative activity

TEST EXAMPLE 2

The concentration of Acid ureases A, B, F, G and H obtained by Examples 1, 2, 6, 7 and 8 and Jack bean urease was adjusted to 10 U/ml, and these enzyme activites were assayed in the presence of 20% ethanol at 20° C.

The results are shown in Table 19.

TABLE 19

| Acid urease | Relative activity (%) |
|---|---|
| Acid urease A | 100.0 |
| Acid urease B | 95.0 |
| Acid urease F | 107.0 |
| Acid urease G | 119.7 |
| Acid urease H | 121.6 |
| Jack bean urease* | 0.5 |

Note: *The urease obtained from Jack bean, optimal pH 7.0, the product of P.L. Biochemicals, Inc., U.S.A.

What we claim is:

1. An acid urease having the following physicochemical properties:
   (1) Action
      It produces 2 moles of ammonia and 1 mole of carbon dioxide gas from 1 mole of urea and 1 mole of water,
   (2) Substrate specificity
      It acts most potently on urea,
   (3) Optimal pH and pH stability
      Its optimal pH is 1.5 to 5.5; it is stable at pH 6–8 at 37° C. for 30 minutes,
   (4) Optimal temperature and temperature stability
      Its optimal temperature at the optimal pH is 55 to 75° C.; at pH 6 it remains stable for 30 minutes up to 50° C.,
   (5) Inhibitors
      It is inhibited by mercuric chloride and acetohydroxamic acid,
   (6) Molecular weight
      Its molecular weight as determined by gel filtration is 100,000 to 250,000, and
   (7) Specific activity
      Its specific activity at the optimal pH and 37° C. is not less than 20 U/mg protein.

2. A method for producing an acid urease having the following physicochemical properties:
   (1) Action
      It produces 2 moles of ammonia and 1 mole of carbon dioxide gas from 1 mole of urea and 1 mole of water,
   (2) Substrate specificity
      It acts most potently on urea,
   (3) Optimal pH and pH stability
      Its optimal pH is 1.5 to 5.5; it is stable at pH 6–8 at 37° C. for 30 minutes,
   (4) Optimal temperature and temperature stability
      Its optimal temperature at the optimal pH is 55 to 75° C.; at pH 6 it remains stable for 30 minutes up to 50° C., (5) Inhibitors It is inhibited by mercuric chloride and acetohydroxamic acid, (6) Molecular weight Its molecular weight as determined by gel filtration is 100,000 to 250,000, and (7) Specific activity Its specific activity at the optimal pH and 37° C. is not less than 20 U/mg protein, which comprises cultivating in a culture medium a microorganism which belongs to the genus Lactobacillus or the genus Streptococcus and is capable of producing the acid urease having the above properties, to thereby cause formation and accumulation of the acid urease in the culture broth, and recovering the acid urease from the culture broth.

3. The method according to claim 2, wherein the microorganism belongs to *Lactobacillus fermentum, Lactobacillus reuteri* or *Lactobacillus ruminis.*

4. The method according to claim 2, wherein the microorganism belongs to *Streptococcus bovis, Streptococcus mitior* or *Streptococcus salivarius.*

5. The method according to claim 3, wherein the microorganism is *Lactobacillus fermentum* JCM 5867 (IFO 14511, FERM BP-1454).

6. The method according to claim 3, wherein the microorganism is *Lactobacillus reuteri* Rt-5 (IFO 14631, FERM BP-1447).

7. The method according to claim 3, wherein the microorganism is *Lactobacillus ruminis* PG-98 (IFO 14632, FERM BP-1906).

8. The method according to claim 3, wherein the microorganism is *Lactobacillus reuteri* UM-12 (IFO 14629, FERM BP-1904).

9. The method according to claim 3, wherein the microorganism is *Lactobacillus reuteri* UM-18 (IFO 14630, FERM BP-1905).

10. The method according to claim 4, wherein the microorganism is *Streptococcus bovis* PG-186 (IFO 14634, FERM BP-1449).

11. The method according to claim 4, wherein the microorganism is *Streptococcus mitior* PG-154 (IFO 14633, FERM BP-1448).

12. The method according to claim 4, wherein the microorganism is *Streptococcus salivarius* PG-303W (IFO 746, FERM BP-1856).

* * * * *